United States Patent
Lukyanov et al.

(10) Patent No.: US 7,150,979 B2
(45) Date of Patent: *Dec. 19, 2006

(54) NUCLEIC ACIDS ENCODING NON-AGGREGATING FLUORESCENT PROTEINS AND METHODS FOR USING THE SAME

(75) Inventors: Sergey Lukyanov, Moscow (RU); Konstantin Lukyanov, Moscow (RU); Yuriy Yanushevich, Moscow (RU); Alexandr Savitsky, Moscow (RU); Arcady Fradkov, Moscow (RU)

(73) Assignee: Clontech Laboratories, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/187,622

(22) Filed: Jul. 21, 2005

(65) Prior Publication Data

US 2006/0035330 A1 Feb. 16, 2006

Related U.S. Application Data

(63) Continuation of application No. 10/081,864, filed on Feb. 20, 2002, now Pat. No. 6,969,597, and a continuation-in-part of application No. 10/006,922, filed on Dec. 4, 2001.

(60) Provisional application No. 60/270,983, filed on Feb. 21, 2001.

(51) Int. Cl.
C12P 21/06 (2006.01)

(52) U.S. Cl. ........................ 435/69.1; 435/6; 435/69.1; 435/320.1; 435/325; 435/7.1; 435/810; 530/350

(58) Field of Classification Search ................ None
See application file for complete search history.

(56) References Cited

U.S. PATENT DOCUMENTS

| | | | |
|---|---|---|---|
| 5,491,084 | A | 2/1996 | Chalfie et al. |
| 5,874,304 | A | 2/1999 | Zolotukhin |
| 5,919,445 | A | 7/1999 | Chao |
| 5,958,713 | A | 9/1999 | Thastrup et al. |
| 5,968,738 | A | 10/1999 | Anderson et al. |
| 5,968,750 | A | 10/1999 | Zolutukhin et al. |
| 5,976,796 | A | 11/1999 | Szalay et al. |
| 5,985,577 | A | 11/1999 | Bulinski |
| 6,020,192 | A | 2/2000 | Muzyczka et al. |
| 6,066,476 | A | 5/2000 | Tsien et al. |
| 6,342,379 | B1 | 1/2002 | Tsien et al. |

FOREIGN PATENT DOCUMENTS

| | | |
|---|---|---|
| WO | 19718640 A1 | 7/1999 |
| WO | WO 99/49019 | 9/1999 |
| WO | WO 00/46233 | 2/2000 |
| WO | WO 00/34319 | 6/2000 |
| WO | WO 00/34320 | 6/2000 |
| WO | WO 00/34321 | 6/2000 |
| WO | WO 00/34322 | 6/2000 |
| WO | WO 00/34323 | 6/2000 |
| WO | WO 00/34324 | 6/2000 |
| WO | WO 00/34325 | 6/2000 |
| WO | WO 00/34326 | 6/2000 |
| WO | WO 01/27150 | 4/2001 |
| WO | WO 00/34318 | 6/2002 |

OTHER PUBLICATIONS

Wells, Biochemistry, vol. 29, pp. 8509-8517, 1990.*
Heim et al. (PNAS, vol. 91, pp. 12501-12504, 1994.*
Lund et al., Biophysical Journal, vol. 85, No. 5, Nov. 2003, pp. 2940-2947.*
Anderluh et al. "Cloning, Sequencing, and Expression of Equinatoxin II," *Biochem. Biophys. Res. Comm.* (1996) 220: 437-442.
Dove et al. "Isolation and Partial Characterization of the Pink and Blue Pigments of Pocilloporid," *Biol. Bull.* (1995) 189: 288-297.
Fradkov et al. "Novel Fluorescent Protein From Discosoma Coral and its Mutants Possesses a Unique Far-Red Fluorescence," *FEBS Letters* (2000) 479: 127-130.
Gurskaya et al. "GFP-Like Chromoproteins as a Source of Far-Red Fluorescent Proteins," *FEBS Letters* (2001) 507: 16-20.
Gurskaya et al. "Color Transitions in Coral's Fluorescent Proteins by Site-Directed Mutagenesis," *BMC biochemistry* (2001) 2:6.
Lukyanov et al. "Natural Animal Coloration can be Determined by a Nonfluorescent Green Fluorescent Protein Homolog," *The Journal of Biological Chemistry* (2000) 275 (34): 25879-25882.
Maček et al. "Intrinsic Tryptophan Fluorescence of Equinatoxin II, a Pore-Forming Polypeptide from the Sea Anemone *Actinia equina* L, Monitors its Interaction with Lipid Membranes," *Eur. J. Biochem.* (1995) 234: 329-335.

(Continued)

*Primary Examiner*—Hope Robinson
(74) *Attorney, Agent, or Firm*—Bret Field; Bozicevic, Field & Francis LLP

(57) ABSTRACT

Nucleic acid compositions encoding non-aggregating chromo/fluoroproteins and mutants thereof, as well as the encoded proteins, are provided. The proteins of interest are polypeptides that are non-aggregating colored and/or fluorescent proteins, where the non-aggregating feature arises from the modulation of residues in the N-terminus of the protein and the chromo and/or fluorescent feature arises from the interaction of two or more residues of the protein. Also provided are fragments of the subject nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

8 Claims, 15 Drawing Sheets

OTHER PUBLICATIONS

Martynov, et al. "Alternative Cyclization in GFP-Like Proteins Family," *Journal of Biological Chemistry* (2001) 276(24): 21012-21016.

Matz et al. "Fluorescent Proteins from Nonbioluminescent Anthozoa Species," *Nature Biotechnology* (1999) 17: 969-973.

Terskikh et al. "'Fluorescent Timer': Protein that Changes Color with Time", *Science* (2000) 290:1585-1588.

Tsein "The Green Fluorescent Protein," *Ann. Rev. Biochem.* (1998) 67: 509-544.

Tsein "Rosy Dawn for Fluorescent Proteins," *Nature Biotechnology* (1999) 17: 956-957.

Ward et al. "An Energy Transfer Protein in Coelenterate Bioluminescence," *J. Bio. Chem.* (1979) 254(4): 781-787.

Wiedenmann et al. "The Ectodermal Pigments of the Morphs of *Anemonia sp.* (*sulcata*) (Pennant)(Cnidaria; Anthozoa): An Adaptation to the Life in Different Depths," *Molecular Biology* (2000) 36(4): 521-528.

Yanushevich et al. "A Strategy for the Generation on Non-Aggregating Mutants of *Anthozoa* Fluorescent Proteins," *FEBS* (2002) 511: 11-14.

Yarbrough et al. "Refined Crystal Structure of DsRed, a Fluorescent Protein from Coral, at 2.0-Resolution," *Proc. Natl. Acad. Sci* (2001) 98(2): 462-467.

R. Wetzel "Mutations and Off-Pathway Aggregation of Proteins," *Tibtech* (1994) 12:193-198.

G. Baird et al. "Biochemistry, Mutagenesis, and Oligometrization of DsRed, a Red Fluorescent Protein from Coral," *Proc. Natl. Acad. Sci* (2000) 97(22):11984-11989.

Wall et al. "The Structural Basis for Red Fluorescence in the Tetrameric GFP Homolog DsRed," *Nature Structural Biology* (2000) 7(12):1133-1138.

Wiehler et al. "Mutants of Discosoma Red Fluorescent Protein with a GFP-Like Chromophore," *FEBS Letter* (2001) 487:384-389.

\* cited by examiner

FIGURE 1 cDNA sequence of wild type amFP486

ATGGCTCTTTCAAACAAGTTTATCGGAGATGACATGAAAATGACCTACCATATGGATG
GCTGTGTCAATGGGCATTACTTTACCGTCAAAGGTGAAGGCAACGGGAAGCCATACGA
AGGGACGCAGACCTCGACTTTTAAAGTCACCATGGCCAACGGTGGGCCCCTTGCATTC
TCCTTTGACATACTATCTACAGTGTTCAAGTATGGAAATCGATGCTTTACTGCGTATC
CTACCAGTATGCCCGACTATTTCAAACAAGCATTTCCTGACGGAATGTCATATGAAAG
GACTTTTACCTATGAAGATGGAGGAGTTGCTACAGCCAGTTGGGAAATAAGCCTTAAA
GGCAACTGCTTTGAGCACAAATCCACGTTTCATGGAGTGAACTTTCCTGCTGATGGAC
CTGTGATGGCGAAGATGACAACTGGTTGGGACCCATCTTTTGAGAAAATGACTGTCTG
CGATGGAATATTGAAGGGTGATGTCACCGCGTTCCTCATGCTGCAAGGAGGTGGCAAT
TACAGATGCCAATTCCACACTTCTTACAAGACAAAAAAACCGGTGACGATGCCACCAA
ACCATGCGGTGGAACATCGCATTGCGAGGACCGACCTTGACAAAGGTGGCAACAGTGT
TCAGCTGACGGAGCACGCTGTTGCACATATAACCTCTGTTGTCCCTTTC (SEQ ID
NO:01)

amino acid sequence of wild type amFP486

MALSNKFIGD DMKMTYHMDG CVNGHYFTVK GEGNGKPYEG TQTSTFKVTM ANGGPLAFSF
DILSTVFKYG NRCFTAYPTS MPDYFKQAFP DGMSYERTFT YEDGGVATAS WEISLKGNCF
EHKSTFHGVN FPADGPVMAK MTTGWDPSFE KMTVCDGILK GDVTAFLMLQ GGGNYRCQFH
TSYKTKKPVT MPPNHAVEHR IARTDLDKGG NSVQLTEHAV AHITSVVPF
 (SEQ ID NO:02)

Figure 2 cDNA sequence of zFP506

ATGGCTCAGTCAAAGCACGGTCTAACAAAAGAAATGACAATGAAATACCGTATGGAAGGGTGC
GTCGATGGACATAAATTTGTGATCACGGGAGAGGGCATTGGATATCCGTTCAAAGGGAAACAG
GCTATTAATCTGTGTGTGGTCGAAGGTGGACCATTGCCATTTGCCGAAGACATATTGTCAGCT
GCCTTTATGTACGGAAACAGGGTTTTCACTGAATATCCTCAAGACATAGCTGACTATTTCAAG
AACTCGTGTCCTGCTGGTTATACATGGGACAGGTCTTTTCTCTTTGAGGATGGAGCAGTTTGC
ATATGTAATGCAGATATAACAGTGAGTGTTGAAGAAAACTGCATGTATCATGAGTCCAAATTT
TATGGAGTGAATTTTCCTGCTGATGGACCTGTGATGAAAAAGATGACAGATAACTGGGAGCCA
TCCTGCGAGAAGATCATACCAGTACCTAAGCAGGGGATATTGAAAGGGGATGTCTCCATGTAC
CTCCTTCTGAAGGATGGTGGGCGTTTACGGTGCCAATTCGACACAGTTTACAAAGCAAAGTCT
GTGCCAAGAAAGATGCCGGACTGGCACTTCATCCAGCATAAGCTCACCCGTGAAGACCGCAGC
GATGCTAAGAATCAGAAATGGCATCTGACAGAACATGCTATTGCATCCGGATCTGCATTGCCC
(SEQ ID NO:03)

amino acid sequence of zFP506

MAQSKHGLTK EMTMKYRMEG CVDGHKFVIT GEGIGYPFKG KQAINLCVVE GGPLPFAEDI LSAAFNYGNR VFTEYPQDIA
DYFKNSCPAG YTWDRSFLFE DGAVCICNAD ITVSVEENCM YHESKFYGVN FPADGPVMKK MTDNWEPSCE KIIPVPKQGI
LKGDVSMYLL LKDGGRLRCQ FDTVYKAKSV PRKMPDWHFI QHKLTREDRS DAKNQKWHLT EHAIASGSAL P
(SEQ ID NO:04)

Figure 3 cDNA sequence of zFP538

```
gagttgagtt tctcgacttc agttgtatca attttggggc atcaagcgat ctattttcaa
catggctcat tcaaagcacg gtctaaaaga agaaatgaca atgaaatacc acatggaagg
gtgcgtcaac ggacataaat ttgtgatcac gggcgaaggc attggatatc cgttcaaagg
gaaacagact attaatctgt gtgtgatcga aggggacca ttgccatttt ccgaagacat
attgtcagct ggctttaagt acggagacag gattttcact gaatatcctc aagacatagt
agactatttc aagaactcgt gtcctgctgg atatacatgg ggcaggtctt ttctctttga
ggatggagca gtctgcatat gcaatgtaga tataacagtg agtgtcaaag aaaactgcat
ttatcataag agcatattta atggaatgaa ttttcctgct gatggacctg tgatgaaaaa
gatgacaact aactgggaag catcctgcga gaagatcatg ccagtaccta agcagggat
actgaaaggg gatgtctcca tgtacctcct tctgaaggat ggtgggcgtt accggtgcca
gttcgacaca gtttacaaag caaagtctgt gccaagtaag atgccggagt ggcacttcat
ccagcataag ctcctccgtg aagaccgcag cgatgctaag aatcagaagt ggcagctgac
agagcatgct attgcattcc cttctgcctt ggcctgataa gaatgtagtt ccaacatttt
aatgcatgtg cttgtcaatt attctgataa aaatgtagtt gagttgaaaa cagacaagta
caaataaagc acatgtaaat cgtct      (SEQ ID NO:05)
``` amino acid sequence of zFP538

```
Met Ala His Ser Lys His Gly Leu Lys Glu Glu Met Thr Met Lys
Tyr His Met Glu Gly Cys Val Asn Gly His Lys Phe Val Ile Thr
Gly Glu Gly Ile Gly Tyr Pro Phe Lys Gly Lys Gln Thr Ile Asn
Leu Cys Val Ile Glu Gly Gly Pro Leu Pro Phe Ser Glu Asp Ile
Leu Ser Ala Gly Phe Lys Tyr Gly Asp Arg Ile Phe Thr Glu Tyr
Pro Gln Asp Ile Val Asp Tyr Phe Lys Asn Ser Cys Pro Ala Gly
Tyr Thr Trp Gly Ser Phe Leu Phe Glu Asp Gly Ala Val Cys Ile
Cys Asn Val Asp Ile Thr Val Ser Val Lys Glu Asn Cys Ile Tyr
His Lys Ser Ile Phe Asn Gly Met Asn Phe Pro Ala Asp Gly Pro
Val Met Lys Lys Met Thr Thr Asn Trp Glu Ala Ser Cys Glu Lys
Ile Met Pro Val Pro Lys Gln Gly Ile Leu Lys Gly Asp Val Ser
Met Tyr Leu Leu Leu Lys Asp Gly Gly Arg Tyr Arg Cys Gln Phe
Asp Thr Val Tyr Lys Ala Lys Ser Val Pro Ser Lys Met Pro Glu
Trp His Phe Ile Gln His Lys Leu Leu Arg Glu Asp Arg Ser Asp
Ala Lys Asn Gln Lys Trp Gln Leu Thr Glu His Ala Ile Ala Phe
Pro Ser Ala Leu Ala   (SEQ ID NO:06)
```

FIGURE 4

All mutants are derived from drFP583 (called "pink" or FP6.) by random mutagenesis The mutants E57 and AG4 are derivative from E5

Mutant: E5 = V105A, S197T Phenotype: in *E.coli* seen as Green overnight, matures to Red over 24h at 37°C (final peaks ratio Red vs. Green is 75:25); folding is faster then FP6.

Mutant: E8 = N42H Phenotype: always has two peaks Green & Red in approx. 60:40; folding is faster than E5 (about 8h at 37°C)

Mutant: E83 = N42H, V71A, I180V Phenotype: always has two almost equal peaks Green & Red; folding is the same as for E8

Mutant: E5up = V105A Phenotype: seen as Red from the beginning; folding is faster than E5 (about 12-16h) Almost no Green peak at final point of maturation Mutant: E57 = V105A, I161T, S197A Phenotype: at common is like E5up but folding is more faster (no more that 8-10h) Very small Green peak at final point of maturation (less that 5%)

Mutant: E5down = S197T Phenotype and folding rate are exactly the same as for E5

Mutant: AG4 = V71M, V105A, S197T Phenotype: Very bright Green, no Red at all (even at the beginning); folding is faster than E5 (no more that 16h)

Mutant: AG4 = V71M, V105A, Y120H, S197T Phenotype: at common is like AG4, but more brighter (appox. twice) one.

```
  1   Met Arg Ser Ser Lys Asn Val Ile Lys Glu Phe Met Arg Phe Lys Val      16
  1   ATG CGC TCC TCC AAG AAC GTC ATC AAG GAG TTC ATG CGC TTC AAG GTG      48

17   Arg Met Glu Gly Thr Val Asn Gly His Glu Phe Glu Ile Glu Gly Glu      32
 49   CGC ATG GAG GGC ACC GTG AAC GGC CAC GAG TTC GAG ATC GAG GGC GAG      96
                                              His(CAC) for E8 and E83
 33   Gly Glu Gly Arg Pro Tyr Glu Gly His Asn Thr Val Lys Leu Lys Val      48
 97   GGC GAG GGC CGC CCC TAC GAG GGC CAC AAC ACC GTG AAG CTG AAG GTG     144

49   Thr Lys Gly Gly Pro Leu Pro Phe Ala Trp Asp Ile Leu Ser Pro Gln      64
145   ACC AAG GGC GGC CCC CTG CCC TTC GCC TGG GAC ATC CTG TCC CCC CAG     192
                        Met(ATG) for AG4 and AG45/Ala(GCG) for E83
 65   Phe Gln Tyr Gly Ser Lys Val Tyr Val Lys His Pro Ala Asp Ile Pro      80
193   TTC CAG TAC GGC TCC AAG GTG TAC GTG AAG CAC CCC GCC GAC ATC CCC     240

81   Asp Tyr Lys Lys Leu Ser Phe Pro Glu Gly Phe Lys Trp Glu Arg Val      96
241   GAC TAC AAG AAG CTG TCC TTC CCC GAG GGC TTC AAG TGG GAG CGC GTG     288
                                 Ala(GCG)-for E5, E57, AG4 and AG45
 97   Met Asn Phe Glu Asp Gly Gly Val Val Thr Val Thr Gln Asp Ser Ser     112
289   ATG AAC TTC GAG GAC GGC GGC GTG GTG ACC GTG ACC CAG GAC TCC TCC     336
                              His(CAC)-for AG45
113   Leu Gln Asp Gly Cys Phe Ile Tyr Lys Val Lys Phe Ile Gly Val Asn     128
337   CTG CAG GAC GGC TGC TTC ATC TAC AAG GTG AAG TTC ATC GGC GTG AAC     384

129   Phe Pro Ser Asp Gly Pro Val Met Gln Lys Lys Thr Met Gly Trp Glu     144
385   TTC CCC TCC GAC GGC CCC GTG ATG CAG AAG AAG ACC ATG GGC TGG GAG     432

145   Ala Ser Thr Glu Arg Leu Tyr Pro Arg Asp Gly Val Leu Lys Gly Glu     160
433   GCC TCC ACC GAG CGC CTG TAC CCC CGC GAC GGC GTG CTG AAG GGC GAG     480
      Thr(ACC) for E57
161   Ile His Lys Ala Leu Lys Leu Lys Asp Gly Gly His Tyr Leu Val Glu     176
481   ATC CAC AAG GCC CTG AAG CTG AAG GAC GGC GGC CAC TAC CTG GTG GAG     528
                Val(GTC) for E83
177   Phe Lys Ser Ile Tyr Met Ala Lys Lys Pro Val Gln Leu Pro Gly Tyr     192
529   TTC AAG TCC ATC TAC ATG GCC AAG AAG CCC GTG CAG CTG CCC GGC TAC     576
                  Thr(ACC) for E5, AG4 and AG45/Ala(GCC) for E57
193   Tyr Tyr Val Asp Ser Lys Leu Asp Ile Thr Ser His Asn Glu Asp Tyr     208
577   TAC TAC GTG GAC TCC AAG CTG GAC ATC ACC TCC CAC AAC GAG GAC TAC     624

209 Thr Ile Val Glu Gln Tyr Glu Arg Thr Glu Gly Arg His His Leu Phe Leu *** 229
625 ACC ATC GTG GAG CAG TAC GAG CGC ACC GAG GGC CGC CAC CAC CTG TTC CTG TAA 678
(SEQ ID NO:07 & 8)
```

FIGURE 5

Amino Acid and Nucleotide Sequence for asFP600

ATGGCTTCCTTTTTAAAGAAGACTATGCCCTTTAAGACGACCATTGAAGGGACGGTTAATGGCCAC
TACTTCAAGTGTACAGGAAAAGGAGAGGGCAACCCATTTGAGGGTACGCAGGAAATGAAGATAGAG
GTCATCGAAGGAGGTCCATTGCCATTTGCCTTCCACATTTTGTCAACGAGTTGTATGTACGGTAGT
AAGGCCTTCATCAAGTATGTGTCAGGAATTCCTGACTACTTCAAGCAGTCTTTCCCTGAAGGTTTT
ACTTGGGAAAGAACCACAACCTACGAGGATGGAGGCTTTCTTACAGCTCATCAGGACACAAGCCTA
GATGGAGATTGCCTCGTTTACAAGGTCAAGATTCTTGGTAATAATTTTCCTGCTGATGGCCCCGTG
ATGCAGAACAAAGCAGGAAGATGGGAGCCATCCACCGAGATAGTTTATGAAGTTGACGGTGTCCTG
CGTGGACAGTCTTTGATGGCCCTTAAGTGCCCTGGTGGTCGTCATCTGACTTGCCATCTCCATACT
ACTTACAGGTCCAAAAAACCAGCTGCTGCCTTGAAGATGCCAGGATTTCATTTTGAAGATCATCGC
ATCGAGATAATGGAGGAAGTTGAGAAAGGCAAGTGCTATAAACAGTACGAAGCAGCAGTGGGCAGG
TACTGTGATGCTGCTCCATCCAAGCTTGGACATAAC (SEQ ID NO:09)

Amino acid

MASFLKKTMP FKTTIEGTVN GHYFKCTGKG EGNPFEGTQE MKIEVIEGGP LPFAFHILST
SCMYGSKTFI KYVSGIPDYF KQSFPEGFTW ERTTTYEDGG FLTAHQDTSL DGDCLVYKVK
ILGNNFPADG PVMQNKAGRW EPATEIVYEV DGVLRGQSLM ALKCPGGRHL TCHLHTTYRS
KKPAAALKMP GFHFEDHRIE IMEEVEKGKC YKQYEAAVGR YCDAAPSKLG HN (SEQ ID
NO:10)

Figure 6

Sequence of humanized 6/9 hybrid gene and 6/9-Q3 mutant

```
                                    for 6/9-2G and 6/9-Q3  CAG(Q)
  1  ATG AGC TGC AGC AAG AAC GTG ATC AAG GAG TTC ATG CGG TTC AAG GTG     48
  1   M   S   C   S   K   N   V   I   K   E   F   M   R   F   K   V     16

49  CGG ATG GAG GGC ACC GTG AAC GGC CAC GAG TTC GAG ATC AAG GGC GAG     96
 17   R   M   E   G   T   V   N   G   H   E   F   E   I   K   G   E     32

97  GGC GAG GGC CGG CCC TAC GAG GGC CAC TGC AGC GTG AAG CTC ATG GTG    144
 33   G   E   G   R   P   Y   E   G   H   C   S   V   K   L   M   V     48

145  ACC AAG GGC GGC CCC CTC CCC TTC GCC TTC GAC ATC CTC AGC CCC CAG    192
 49   T   K   G   G   P   L   P   F   A   F   D   I   L   S   P   Q     64

193  TTC CAG TAC GGC AGC AAG GTG TAC GTG AAG CAC CCC GCC GAC ATC CCC    240
 65   F   Q   Y   G   S   K   V   Y   V   K   H   P   A   D   I   P     80

ATG(M) for 6/9-Q3
241  GAC TAC AAG AAG CTC AGC TTC CCC GAG GGC TTC AAG TGG GAG CGG GTG    288
 81   D   Y   K   K   L   S   F   P   E   G   F   K   W   E   R   V     96

289  ATG AAC TTC GAG GAC GGC GGC GTG GTG ACC GTG AGC CAG GAC AGC AGC    336
 97   M   N   F   E   D   G   G   V   V   T   V   S   Q   D   S   S    112

337  CTC AAG GAC GGC TGC TTC ATC TAC GAG GTG AAG TTC ATC GGC GTG AAC    384
113   L   K   D   G   C   F   I   Y   E   V   K   F   I   G   V   N    128

385  TTC CCC AGC GAC GGC CCC GTG ATG CAG CGG CGG ACC CGG GGC TGG GAG    432
129   F   P   S   D   G   P   V   M   Q   R   R   T   R   G   W   E    144

433  GCC AGC AGC GAG CGG CTC TAC CCC CGG GAC GGC GTG CTC AAG GGC GAC    480
145   A   S   S   E   R   L   Y   P   R   D   G   V   L   K   G   D    160

481  ATC CAC ATG GCC CTC CGG CTC GAG GGC GGC GGC CAC TAC CTC GTG GAG    528
161   I   H   M   A   L   R   L   E   G   G   G   H   Y   L   V   E    176

529  TTC AAG AGC ATC TAC ATG GCC AAG AAG CCC GTG CAG CTC CCC GGC TAC    576
177   F   K   S   I   Y   M   A   K   K   P   V   Q   L   P   G   Y    192

577  TAC TAC GTG GAC AGC AAG CTC GAC ATC ACC AGC CAC AAC GAG GAC TAC    624
193   Y   Y   V   D   S   K   L   D   I   T   S   H   N   E   D   Y    208
                                         TCC(S) for 6/9-2G and 6/9-Q3
625  ACC ATC GTG GAG CAG TAC GAG CGG ACC GAG GGC CGG CAC CAC CTC TTC    672
209   T   I   V   E   Q   Y   E   R   T   E   G   R   H   H   L   F    224

673  CTC TGA                                                            678
225   L   *                                                             226
```

(SEQ ID NO:11 & 12)

Figure 7

Nucleic acid sequence FP6 (E57)-NA

ATGGCCTCCTCCGAGAACGTCATCACCGAGTTCATGCGCTTCAAGGTGCGCATGGAGGGCACCGTGA
ACGGCCACGAGTTCGAGATCGAGGGCGAGGGCGAGGGCCGCCCCTACGAGGGCCACAACACCGTG
AAGCTGAAGGTGACCAAGGGCGGCCCCCTGCCCTTCGCCTGGGACATCCTGTCCCCCCAGTTCCAGT
ACGGCTCCAAGGTGTACGTGAAGCACCCCGCCGACATCCCCGACTACAAGAAGCTGTCCTTCCCCGA
GGGCTTCAAGTGGGAGCGCGTGATGAACTTCGAGGACGGCGGCGTGGCGACCGTGACCCAGGACTC
CTCCCTGCAGGACGGCTGCTTCATCTACAAGGTGAAGTTCATCGGCGTGAACTTCCCCTCCGACGGC
CCCGTGATGCAGAAGAAGACCATGGGCTGGGAGGCCTCCACCGAGCGCCTGTACCCCGCGACGGC
GTGCTGAAGGGCGAGACCCACAAGGCCCTGAAGCTGAAGGACGGCGGCCACTACCTGGTGGAGTTC
AAGTCCATCTACATGGCCAAGAAGCCCGTGCAGCTGCCCGGCTACTACTACGTGGACGCCAAGCTGG
ACATCACCTCCCACAACGAGGACTACACCATCGTGGAGCAGTACGAGCGCACCGAGGGCCGCCACCA
CCTGTTCCTG (SEQ ID NO:13)

Figure 8

DNA sequence (ORF) of E5-NA

ATGGCCTCCTCCGAGAACGTCATCACCGAGTTCATGCGCTTCAAGGTGCGCATGGAGGGCACCGTGA
ACGGCCACGAGTTCGAGATCGAGGGCGAGGGCGAGGGCCGCCCCTACGAGGGCCACAACACCGTG
AAGTTGAAGGTGACCAAGGGCGGCCCCCTGCCCTTCGCCTGGGACATCCTGTCCCCCCAGTTCCAGT
ACGGCTCCAAGGTGTACGTGAAGCACCCCGCCGACATCCCCGACTACAAGAAGCTGTCCTTCCCCGA
GGGCTTCAAGTGGGAGCGCGTGATGAACTTCGAGGACGGCGGCGTGGCGACCGTGACCCAGGACTC
CTCCCTGCAGGACGGCTGCTTCATCTACAAGGTGAAGTTCATCGGCGTGAACTTCCCCTCCGACGGC
CCCGTGATGCAGAAGAAGACCATGGGCTGGGAGGCCTCCACCGAGCGCCTGTACCCCGCGACGGC
GTGCTGAAGGGCGAGATCCACAAGGCCCTGAAGCTGAAGGACGGCGGCCACTACCTGGTGGAGTTC
AAGTCCATCTACATGGCCAAGAAGCCCGTGCAGCTGCCCGGCTACTACTACGTGGACACCAAGCTGG
ACATCACCTCCCACAACGAGGACTACACCATCGTGGAGCAGTACGAGCGCACCGAGGGCCGCCACCA
CCTGTTCCTGTAA (SEQ ID NO:14)

Figure 9
Non-aggregating mutant FP3-NA was generated from zFP506-N65M (non-humanized version). In comparison with zFP506-N65M, FP3-NA contains two additional amino acid substitutions - K5E and K10E. Also, one accidental nucleotide substitution was introduced due to PCR mistake (double underline).

Cloning into pQE30 was done using BamHI and HindIII sites:

```
GGA TCC GCT CAG TCA GAG CAC GGT CTA ACA GAA GAA ATG ACA ATG AAA
BamHI  A   Q   S   E   H   G   L   T   E   E   M   T   M   K

TAC CGT ATG GAA GGG TGC GTC GAT GGA CAT AAA TTT GTG ATC ACG GGA
 Y   R   M   E   G   C   V   D   G   H   K   F   V   I   T   G

GAG GGC ATT GGA TAT CCG TTC AAA GGG AAA CAG GCT ATT AAT CTG TGT
 E   G   I   G   Y   P   F   K   G   K   Q   A   I   N   L   C

GTG GTC GAA GGT GGA CCA TTG CCA TTT GCC GAA GAC ATA TTG TCA GCT
 V   V   E   G   G   P   L   P   F   A   E   D   I   L   S   A

GCC TTT ATG TAC GGA AAC AGG GTT TTC ACT GAA TAT CCT CAA GAC ATA
 A   F   M   Y   G   N   R   V   F   T   E   Y   P   Q   D   I

GTT GAC TAT TTC AAG AAC TCG TGT CCT GCT GGA TAT ACA TGG GAC AGG
 V   D   Y   F   K   N   S   C   P   A   G   Y   T   W   D   R

TCT TTT CTC TTT GAG GAT GGA GCA GTT TGC ATA TGT AAT GCA GAT ATA
 S   F   L   F   E   D   G   A   V   C   I   C   N   A   D   I

ACA GTG AGT GTT GAA GAA AAC TGC ATG TAT CAT GAG TCC AAA TTC TAT
 T   V   S   V   E   E   N   C   M   Y   H   E   S   K   F   Y

GGA GTG AAT TTT CCT GCT GAT GGA CCT GTG ATG AAA AAG ATG ACA GAT
 G   V   N   F   P   A   D   G   P   V   M   K   K   M   T   D

AAC TGG GAG CCA TCC TGC GAG AAG ATC ATA CCA GTA CCT AAG CAG GGG
 N   W   E   P   S   C   E   K   I   I   P   V   P   K   Q   G

ATA TTG AAA GGG GAT GTC TCC ATG TAC CTC CTT CTG AAG GAT GGT GGG
 I   L   K   G   D   V   S   M   Y   L   L   L   K   D   G   G

CGT TTA CGG TGC CAA TTC GAC ACA GTT TAC AAA GCA AAG TCT GTG CCA
 R   L   R   C   Q   F   D   T   V   Y   K   A   K   S   V   P

AGA AAG ATG CCG GAC TGG CAC TTC ATC CAG CAT AAG CTC ACC CGT GAA
 R   K   M   P   D   W   H   F   I   Q   H   K   L   T   R   E

GAC CGC AGC GAT GCT AAG AAT CAG AAA TGG CAT CTG ACA GAA CAT GCT
 D   R   S   D   A   K   N   Q   K   W   H   L   T   E   H   A

ATT GCA TCC GGA TCT GCA TTG CCC TGA AAGCTT
 I   A   S   G   S   A   L   P   *   HindIII   (SEQ ID NO:15 & 16)
```

Figure 10
Non-aggregating mutant FP4-NA was generated from zFP538-M128V (humanized version). In comparison with zFP538-M128V, FP4-NA contains two additional amino acid substitutions - K5E and K9T. Also, two accidental nucleotide substitutions were introduced due to PCR mistakes (double underline).

Cloning into pQE30 was done using BamHI and HindIII sites:

```
GGA TCC GCC CAC AGC GAG CAC GGC CTG ACC GAG GAG ATG ACC ATG AAG
BamHI    A   H   S   E   H   G   L   T   E   E   M   T   M   K

TAC CAC ATG GAG GGC TGC GTG AAC GGC CAC AAG TTC GTG ATC ACC GGC
 Y   H   M   E   G   C   V   N   G   H   K   F   V   I   T   G

GAG GGC ATC GGC TAC CCC TTC AAG GGC AAG CAG ACC ATC AAC CTG TGC
 E   G   I   G   Y   P   F   K   G   K   Q   T   I   N   L   C

GTG ATC GAG GGC GGC CCC CTG CCC TTC AGC GAG GAC ATC CTG AGC GCC
 V   I   E   G   G   P   L   P   F   S   E   D   I   L   S   A

GGC TTC AAG TAC GGC GAC CGG ATC TTC ACC GAG TAC CCC CAG GAC ATC
 G   F   K   Y   G   D   R   I   F   T   E   Y   P   Q   D   I

GTG GAC TAC TTC AAG AAC AGC TGC CCC GCC GGC TAC ACC TGG GGC CGG
 V   D   Y   F   K   N   S   C   P   A   G   Y   T   W   G   R

AGC TTC CTG TTC GAG GAC GGC GCC GTG TGC ATC TGT AAC GTG GAC ATC
 S   F   L   F   E   D   G   A   V   C   I   C   N   V   D   I

ACC GTG AGC GTG AAG GAG AAC TGC ATC TAC CAC AAG AGC ATC TTC AAC
 T   V   S   V   K   E   N   C   I   Y   H   K   S   I   F   N

GGC GTG AAC TTC CCC GCC GAC GGC CCC GTG ATG AAG AAG ATG ACC ACC
 G   V   N   F   P   A   D   G   P   V   M   K   K   M   T   T

AAC TGG GAG GCC AGC TGC GAG AAG ATC ATG CCC GTG CCT AAG CAG GGC
 N   W   E   A   S   C   E   K   I   M   P   V   P   K   Q   G

ATC CTG AAG GGC GAC GTG AGC ATG TAC CTG CTG CTG AAG GAC GGC GGC
 I   L   K   G   D   V   S   M   Y   L   L   L   K   D   G   G

CGG TAC CGG TGC CAG TTC GAC ACC GTG TAC AAG GCC AAG AGC GTG CCC
 R   Y   R   C   Q   F   D   T   V   Y   K   A   K   S   V   P

AGC AAG ATG CCC GAG TGG CAC TTC ATC CAG CAC AAG CTG CTG CGG GAG
 S   K   M   P   E   W   H   F   I   Q   H   K   L   L   R   E

GAC CGG AGC GAC GCC AAG AAC CAG AAG TGG CAG CTG ACC GAG CAC GCC
 D   R   S   D   A   K   N   Q   K   W   Q   L   T   E   H   A

ATC GCC TTC CCC AGC GCC CTG GCC TGA AAGCTT
 I   A   F   P   S   A   L   A   *   HindIII          (SEQ ID NOS: 17 & 18)
```

Figure 11

```
            M   A   L   S   N   E   F   I   G   D   D   M   K   M
676     ATG GCC CTG TCC AAC GAG TTC ATC GGC GAC GAC ATG AAG ATG
        TAC CGG GAC AGG TTG CTC AAG TAG CCG CTG CTG TAC TTC TAC
        T   Y   H   M   D   G   C   V   N   G   H   Y   F   T   V
721     ACC TAC CAC ATG GAC GGC TGC GTG AAC GGC CAC TAC TTC ACC GTG
        TGG ATG GTG TAC CTG CCG ACG CAC TTG CCG GTG ATG AAG TGG CAC
        K   G   E   G   S   G   K   P   Y   E   G   T   Q   T   S
766     AAG GGC GAG GGC AGC GGC AAG CCC TAC GAG GGC ACC CAG ACC TCC
        TTC CCG CTC CCG TCG CCG TTC GGG ATG CTC CCG TGG GTC TGG AGG
        T   F   K   V   T   M   A   N   G   G   P   L   A   F   S
811     ACC TTC AAG GTG ACC ATG GCC AAC GGC GGC CCC CTG GCC TTC TCC
        TGG AAG TTC CAC TGG TAC CGG TTG CCG CCG GGG GAC CGG AAG AGG
        F   D   I   L   S   T   V   F   M   Y   G   N   R   C   F
856     TTC GAC ATC CTG TCC ACC GTG TTC ATG TAC GGC AAC CGC TGC TTC
        AAG CTG TAG GAC AGG TGG CAC AAG TAC ATG CCG TTG GCG ACG AAG
        T   A   Y   P   T   S   M   P   D   Y   F   K   Q   A   F
901     ACC GCC TAC CCC ACC AGC ATG CCC GAC TAC TTC AAG CAG GCC TTC
        TGG CGG ATG GGG TGG TCG TAC GGG CTG ATG AAG TTC GTC CGG AAG
        P   D   G   M   S   Y   E   R   T   F   T   Y   E   D   G
946     CCC GAC GGC ATG TCC TAC GAG AGA ACC TTC ACC TAC GAG GAC GGC
        GGG CTG CCG TAC AGG ATG CTC TCT TGG AAG TGG ATG CTC CTG CCG
        G   V   A   T   A   S   W   E   I   S   L   K   G   N   C
991     GGC GTG GCC ACC GCC AGC TGG GAG ATC AGC CTG AAG GGC AAC TGC
        CCG CAC CGG TGG CGG TCG ACC CTC TAG TCG GAC TTC CCG TTG ACG
        F   E   H   K   S   T   F   H   G   V   N   F   P   A   D
1036    TTC GAG CAC AAG TCC ACC TTC CAC GGC GTG AAC TTC CCC GCC GAC
        AAG CTC GTG TTC AGG TGG AAG GTG CCG CAC TTG AAG GGG CGG CTG
        G   P   V   M   A   K   K   T   T   G   W   D   P   S   F
1081    GGC CCC GTG ATG GCC AAG AAG ACC ACC GGC TGG GAC CCC TCC TTC
        CCG GGG CAC TAC CGG TTC TTC TGG TGG CCG ACC CTG GGG AGG AAG
        E   K   M   T   V   C   D   G   I   L   K   G   D   V   T
1126    GAG AAG ATG ACC GTG TGC GAC GGC ATC TTG AAG GGC GAC GTG ACC
        CTC TTC TAC TGG CAC ACG CTG CCG TAG AAC TTC CCG CTG CAC TGG
        A   F   L   M   L   Q   G   G   G   N   Y   R   C   Q   F
1171    GCC TTC CTG ATG CTG CAG GGC GGC GGC AAC TAC AGA TGC CAG TTC
        CGG AAG GAC TAC GAC GTC CCG CCG CCG TTG ATG TCT ACG GTC AAG
        H   T   S   Y   K   T   K   K   P   V   T   M   P   P   N
1216    CAC ACC TCC TAC AAG ACC AAG AAG CCC GTG ACC ATG CCC CCC AAC
        GTG TGG AGG ATG TTC TGG TTC TTC GGG CAC TGG TAC GGG GGG TTG
        H   V   V   E   H   R   I   A   R   T   D   L   D   K   G
1261    CAC GTG GTG GAG CAC CGC ATC GCC AGA ACC GAC CTG GAC AAG GGC
        GTG CAC CAC CTC GTG GCG TAG CGG TCT TGG CTG GAC CTG TTC CCG
        G   N   S   V   Q   L   T   E   H   A   V   A   H   I   T
1306    GGC AAC AGC GTG CAG CTG ACC GAG CAC GCC GTG GCC CAC ATC ACC
        CCG TTG TCG CAC GTC GAC TGG CTC GTG CGG CAC CGG GTG TAG TGG
        S   V   V   P   F   *
1351    TCC GTG GTG CCC TTC TGA
        AGG CAC CAC GGG AAG ACT        (SEQ ID NO:19 & 20)
```

Figure 12

Non-aggregating mutant FP7-NA was generated from M35-5 (FP7a). In comparison with M35-5, FP7-NA contains two additional substitutions - K6T and K7E. Nucleotide substitutions in the codon for Leu-4 were introduced to optimize codon usage (double underline).

Cloning into pQE30 was done using BamHI and HindIII sites:

```
GGA TCC GCC TCC CTG CTG ACC GAG ACC ATG CCC TTC AGG ACC ACC ATC
BamHI  A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D

GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC CTG
 T   E   I   V   Y   E   V   D   G   V   L   R   G   Q   S   L

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC TGAAGCTT
 A   A   P   S   K   L   G   H   N   *  HindIII  (SEQ ID NO:21 & 22)
```

Figure 13

Dimeric mutant AsRed M35-5D (in comparison to M355NA it carries one amino acid substitution L166S according to GFP numbering; L159S according to self-numbering)

```
ATG GCC TCC CTG CTG ACC GAG ACC ATG CCC TTC AGG ACC ACC ATC
 M   A   S   L   L   T   E   T   M   P   F   R   T   T   I

GAG GGC ACC GTG AAC GGC CAC TAC TTC AAG TGC ACC GGC AAG GGC GAG
 E   G   T   V   N   G   H   Y   F   K   C   T   G   K   G   E

GGC AAC CCC CTC GAG GGC ACC CAG GAG ATG AAG ATC GAG GTG ATC GAG
 G   N   P   L   E   G   T   Q   E   M   K   I   E   V   I   E

GGC GGC CCC CTG CCC TTC GCC TTC CAC ATC CTG TCC ACC TCC TGC ATG
 G   G   P   L   P   F   A   F   H   I   L   S   T   S   C   M

TAC GGC TCC AAG GCC TTC ATC AAG TAC GTG TCC GGC ATC CCC GAC TAC
 Y   G   S   K   A   F   I   K   Y   V   S   G   I   P   D   Y

TTC AAG CAG TCC CTC CCC GAG GGC TTC ACC TGG GAG CGC ACC ACC ACC
 F   K   Q   S   L   P   E   G   F   T   W   E   R   T   T   T

TAC GAG GAC GGC GGC TTC CTG ACC GCC CAC CAG GAC ACC TCC CTG GAC
 Y   E   D   G   G   F   L   T   A   H   Q   D   T   S   L   D

GGC GAC TGC CTG GTG TAC AAG GTG AAG ATC CTG GGC AAC AAC TTC CCC
 G   D   C   L   V   Y   K   V   K   I   L   G   N   N   F   P

GCC GAC GGC CCC GTG ATG CAG AAC AAG GCC GGC CGC TGG GAG CCC TCC
 A   D   G   P   V   M   Q   N   K   A   G   R   W   E   P   S

ACC GAG ATC GTG TAC GAG GTG GAC GGC GTG CTG CGC GGC CAG TCC AGC
 T   E   I   V   Y   E   V   D   G   V   L   R   G   Q   S   S

ATG GCC CTG GAG TGC CCC GGC GGT CGC CAC CTG ACC TGC CAC CTG CAC
 M   A   L   E   C   P   G   G   R   H   L   T   C   H   L   H

ACC ACC TAC CGC TCC AAG AAG CCC GCC TCC GCC CTG AAG ATG CCC GGC
 T   T   Y   R   S   K   K   P   A   S   A   L   K   M   P   G

TTC CAC TTC GAG GAC CAC CGC ATC GAG ATC CTG GAG GAG GTG GAG AAG
 F   H   F   E   D   H   R   I   E   I   L   E   E   V   E   K

GGC AAG TGC TAC AAG CAG TAC GAG GCC GCC GTG GGC CGC TAC TGC GAC
 G   K   C   Y   K   Q   Y   E   A   A   V   G   R   Y   C   D

GCC GCC CCC TCC AAG CTG GGC CAC AAC TGA
 A   A   P   S   K   L   G   H   N   *
```
(SEQ ID NO:23 & 24)

(SEQ ID NOS:25-30)

NUCLEIC ACIDS ENCODING NON-AGGREGATING FLUORESCENT PROTEINS AND METHODS FOR USING THE SAME

CROSS REFERENCE TO RELATED APPLICATIONS

This application is a continuation of U.S. application Ser. No. 10/081,864 filed on Feb. 20, 2002 now U.S. Pat. No. 6,969,597 which claims benefit to U.S. provisional Application No. 60/270,983 filed on Feb. 21, 2001 and is a continuation-in-part of application Ser. No. 10/006,922 filed on Dec. 4, 2001; the disclosures of which applications are incorporated in their entirety herein.

INTRODUCTION

1. Field of the Invention

The field of this invention is chromoproteins and fluorescent proteins.

2. Background of the Invention

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

An important new class of fluorescent proteins that have recently been developed are the Reef Coral Fluorescent Proteins, as described in Matz, M. V., et al. (1999) Nature Biotechnol., 17:969–973. While these fluorescent proteins exhibit many positive attributes, certain versions are prone to high molecular weight aggregation, which can pose problems and consequently limit their applicability.

As such, there is intense interest in the development of non-aggregating versions of this important new class of fluorescent proteins. The present invention satisfies this need.

Relevant Literature

U.S. patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., Biochemical and Biophysical Research Communications (1996) 220:437–442; Dove et al., Biological Bulletin (1995) 189:288–297; Fradkov et al., FEBS Lett. (2000) 479(3):127–30; Gurskaya et al., FEBS Lett., (2001) 507(1):16–20; Gurskaya et al., BMC Biochem. (2001) 2:6; Lukyanov, K., et al (2000) J Biol Chemistry 275(34): 25879–25882; Macek et al., Eur. J. Biochem. (1995) 234: 329–335; Martynov et al., J Biol. Chem. (2001) 276:21012–6; Matz, M. V., et al. (1999) Nature Biotechnol., 17:969–973; Terskikh et al., Science (2000) 290:1585–8; Tsien, Annual Rev. of Biochemistry (1998) 67:509–544; Tsien, Nat. Biotech. (1999) 17:956–957; Ward et al., J. Biol. Chem. (1979) 254:781–788; Wiedermann et al., Jarhrestagung der Deutschen Gesellschact fur Tropenokologie-gto. Ulm. 17–19.02.1999. Poster P-4.20; Yanushevich et al., FEBS Lett (Jan. 30, 2002) 511(1–3):11–4; and Yarbrough et al., Proc Natl Acad Sci U S A (2001) 98:462–7.

SUMMARY OF THE INVENTION

Nucleic acid compositions encoding non-aggregating chromo/fluoroproteins and mutants thereof, as well as the proteins encoded by the same, are provided. The proteins of interest are polypeptides that are non-aggregating colored and/or fluorescent proteins, where the the non-aggregating feature arises from the modulation of residues in the N-terminus of the protein and the chromo and/or fluorescent feature arises from the interaction of two or more residues of the protein. Also provided are fragments of the subject nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

BRIEF DESCRIPTION OF THE FIGURES

FIG. 1 provides the nucleotide and amino acid sequence of wild type amFP486 (NFP-1). (SEQ ID NO:01 & 02)

FIG. 2 provides the nucleotide and amino acid sequence of wild type zFP506 (NFP-3). (SEQ ID NO:03 & 04)

FIG. 3 provides the nucleotide and amino acid sequence of wild type zFP538 (NFP-4). (SEQ ID NO:05 & 06)

FIG. 4 provides the nucleotide and amino acid sequence of wild type drFP583 (NFP-6). (SEQ ID NO: 07 & 08); as well as the nucleotide and amino acid sequence of an alternative version thereof.

FIG. 5 provides the nucleotide and amino acid sequence of wild type asFP600 (NFP-7). (SEQ ID NO:09 & 10)

FIG. 6 provides the nucleotide and amino acid sequence of 6/9Q hybrid protein. (SEQ ID NO:11 & 12)

FIG. 7 provides the nucleotide sequence of mutant E57-NA (DsRED2) (SEQ ID NO:13)

FIG. 8 provides the nucleotide sequence of mutant E5-NA (Timer NA). (SEQ ID NO:14)

FIG. 9 provides the nucleotide and amino acid sequence of FP3-NA (SEQ ID NO:15 & 16)

FIG. 10 provides the nucleotide and amino acid sequence of NFP4-NA (SEQ ID NO:17 & 18).

FIG. 11 provides the nucleotide and amino acid sequence of mut32-NA (SEQ ID NO:19 & 20)

FIG. 12 provides the nucleotide and amino acid sequence of mutant FP7-NA (SEQ ID NO:21 & 22).

FIG. 13 provides the nucleotide and amino acid sequence of mutant FP7-NA dimer. (SEQ ID NO:23 & 24).

M129V-NA; 11—amFP486 mutant K68M; 12—amFP486-K68M-NA; 13—asFP595 mutant M35-5; 14—M35-5-NA; 15—EGFP.

Figure 16:
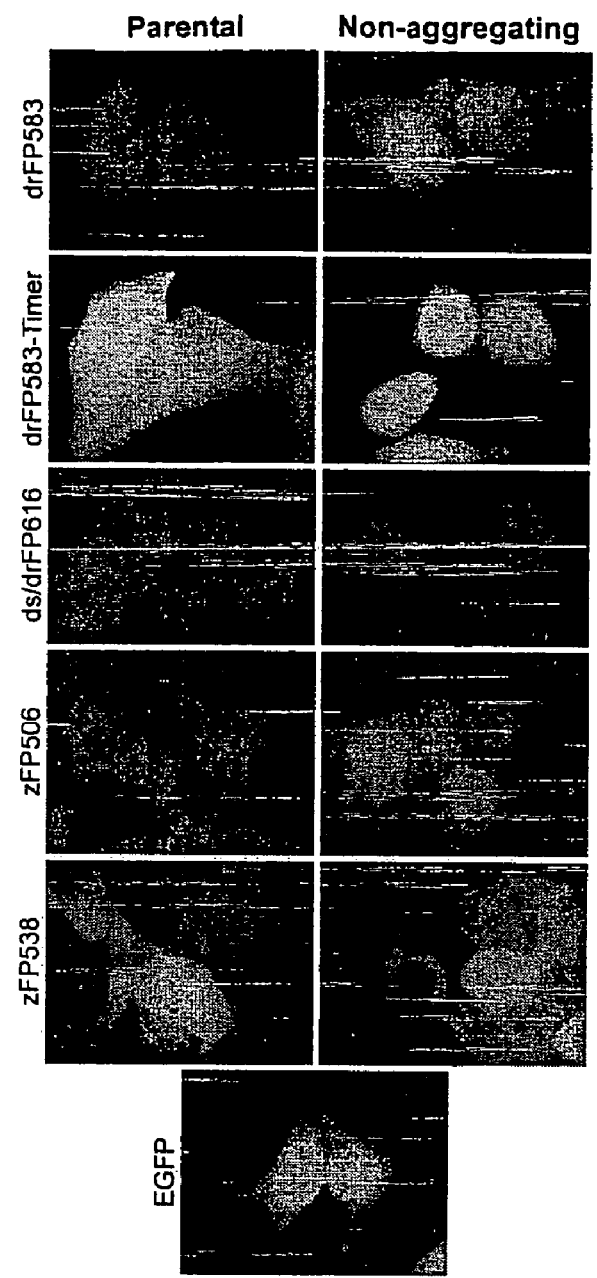

FIG. 16. Fluorescence images of cells expressing parental (left column) and corresponding non-aggregating (right column) fluorescent proteins (see Table 2 for details). Protein names are shown on the left. EGFP-expressing cells are shown for comparison (below) as a well-known non-aggregating fluorescent protein.

DEFINITIONS

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552–59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651–681. New York: Academic Press.; Wilson, T. and Hastings, J. W. (1998). Bioluminescence. *Annu Rev Cell Dev Biol* 14, 197–230). Bioluminescence does not include so-called ultra-weak light emission, which can be detected in virtually all living structures using sensitive luminometric equipment (Murphy, M. E. and Sies, H. (1990). Visible-range low-level chemiluminescence in biological systems. *Meth. Enzymol.* 186, 595–610; Radotic, K, Radenovic, C, Jeremic, M. (1998.) Spontaneous ultra-weak bioluminescence in plants: origin, mechanisms and properties. *Gen Physiol Biophys* 17, 289–308), and from weak light emission which most probably does not play any ecological role, such as the glowing of bamboo growth cone (Totsune, H., Nakano, M., Inaba, H. (1993). Chemiluminescence from bamboo shoot cut. *Biochem. Biophys. Res Comm.* 194, 1025–1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med.* 149, 938–953; Schomer, B. and Epel, D. (1998). Redox changes during fertilization and maturation of marine invertebrate eggs. *Dev Biol* 203, 1–11).

DESCRIPTION OF THE SPECIFIC EMBODIMENTS

Nucleic acid compositions encoding non-aggregating chromo/fluoroproteins and mutants thereof, as well as the encoded proteins, are provided. The proteins of interest are non-aggregating proteins that are colored and/or fluorescent, where the non-aggregating feature arises from the modulation of residues in the N-terminus of the proteins and the chromo and/or fluorescent feature arises from the interaction of two or more residues of the protein. Also of interest are proteins that are substantially similar to, or mutants of, the above specific proteins. Also provided are fragments of the nucleic acids and the peptides encoded thereby, as well as antibodies to the subject proteins, and transgenic cells and organisms that include the subject nucleic acid/protein compositions. The subject protein and nucleic acid compositions find use in a variety of different applications. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications which might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding non-aggregating chromo- and fluoroproteins and mutants thereof, as well as fragments and homologues of these proteins.

As summarized above, the proteins encoded by the subject nucleic acids are non-aggregating chromo and/or fluorescent proteins. By non-aggregating is meant that the proteins do not aggregate, i.e. complex with each other form high molecular weight aggregates. As used herein, an "aggregate" refers to a higher order molecular complex, e.g., a complex that comprises two or more tetramers of the protein. The molecular weight of such aggregates typically exceeds about 100 kDa, and more typically about 150 kDa. Aggregates are distinguished from mulitimers, where the term "multimer" refers to oligomers, such as dimers, trimers, and tetramers. Non-aggregating polypeptides of the subject invention include polypeptides that show reduced aggregation in vitro and/or in vivo as compared to their corresponding aggregating analogues, e.g., corresponding wild type proteins.

In certain embodiments, the subject polypeptides show decreased aggregation in vitro relative to their corresponding aggregating analogues, e.g., their corresponding wild type proteins. "Reduced aggregation in vitro" refers to reduced aggregation in a cell-free system or in solution. In some embodiments, the non-aggregating polypeptide shows less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by the corresponding aggregating analogue under the same in vitro conditions, e.g., less than about 60%, less than about 50%, less than about 40%, less than about 30%, less than about 20%, less than about 10%, or less than about 5%, of the subject polypeptide present in a sample is aggregated. In vitro conditions suitable for comparing a subject polypeptide with its corresponding aggregating analogue are conditions that do not prevent aggregation of the aggregating analogue, e.g., standard physiological conditions. Any of a wide variety of buffer systems used in the art to study physiological phenomena can be used for in vitro comparisons. Non-limiting examples of such conditions include, but are not limited to, a salt concentration in the range of from about 0.01 mM to about 0.1 mM; a temperature in the range of from about 19° C. to about 25° C.; and a pH in the range of from about 6.5 to about 8.0. Buffers that are suitable for comparison of aggregation include, but are not limited to, any physiological buffer; Tris-Cl, phosphate buffered saline; Tris buffered saline; borate buffered saline; and the like. An example is 1×Tris-Cl buffer, pH 8.8, 0.1% SDS, room temperature. An exemplary assay for determining whether a DsRed mutant of the invention forms aggregates is as described in the Examples. In brief, a standard sodium dodecyl sulfate-polyacrylamide gel electrophoresis (SDS-PAGE) protocol is used to separate DsRed mutant proteins produced recombinantly in a bacterial cell, e.g., *E. coli*. Samples are not boiled before loading onto the gel. Standard conditions for SDS-PAGE are described in *Short Protocols in Molecular Biology*, 4$^{th}$ Ed. 1999, FM Ausubel et al., eds., John Wiley & Sons, Inc. Typically, samples are electrophoresed in the presence of about 0.1% SDS in 1×Tris-Cl buffer (pH about 8.8).

In some embodiments, a subject non-aggregating polypeptide exhibits reduced aggregation in vivo. "Reduced aggregation in vivo" refers to reduced aggregation in a cell. In some embodiments, the non-aggregating polypeptide shows less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by its corresponding aggregating analogue under the same in vivo conditions, e.g., in another eukaryotic cell from the same cell line, in an identical prokaryotic cell, or in a eukaryotic cell or cell population of the same cell type. In general, less than about 60%, less than about 50%, less than about 40%, less than about 30%, less than about 20%, less than about 10%, or less than about 5%, of the subject non-aggregating polypeptide present in a cell or a cell population is aggregated. Methods of measuring the degree of aggregation are known in the art; any known method can be used to determine whether a given mutant shows a reduction in aggregation compared to corresponding aggregating analogue, e.g., when compared to a corresponding aggregating wild type polypeptide. Such methods include, but are not limited to, "pseudo-native" protein gel electrophoresis, as described in the Examples; gel filtration; ultracentrifugation; circular dichroism; and light scattering. Aggregation can be measured by light scattering, as described in the Examples. For non-aggregated proteins, the ratio of absorption at a shorter wavelength to the absorption at a longer wavelength is close to zero. In some embodiments, the ratio of absorption at 400 nm to the absorption at 566 nm of a non-aggregating polypeptide is in the range of from about 0.01 to about 0.1, from about 0.015 to about 0.09, from about 0.02 to about 0.08, from about 0.025 to about 0.07, or from about 0.03 to about 0.06.

In many embodiments, the non-aggregating polypeptides of the present invention have amino acid sequences that differ from their corresponding wild type sequences by a mutation in the N-terminus that modulates the charges appearing on side groups of the N-terminus residues, e.g., to reverse or neutralize the charge, in a manner sufficient to produce a non-aggregating mutant of the naturally occurring protein or aggregating mutant thereof. More specifically, basic residues located near the N-termini of the proteins are substituted, e.g., Lys and Arg residues close to the N-terminus are substituted with negatively charged or neutral residues. By N-terminus is meant within about 50 residues from the N-terminus, often within about 25 residues of the N-terminus and more often within about 15 residues of the N-terminus, where in many embodiments, residue modifications occur within about 10 residues of the N-terminus. Specific residues of interest in many embodiments include: 2, 3, 4, 5, 6, 7, 8, 9 and 10.

As mentioned above, in addition to the non-aggregating feature of the subject polypeptides encoded by the subject nucleic acids, the subject polypeptides are also characterized in that they are colored and/or fluorescence. By chromo and/or fluorescent protein is meant a protein that is colored, i.e., is pigmented, where the protein may or may not be fluorescent, e.g., it may exhibit low, medium or high fluorescence upon irradiation with light of an excitation wavelength. In any event, the subject proteins of interest are those in which the colored characteristic, i.e., the chromo and/or fluorescent characteristic, is one that arises from the interaction of two or more residues of the protein, and not from a single residue, more specifically a single side chain of a single residue, of the protein. As such, fluorescent proteins of the subject invention do not include proteins that exhibit fluorescence only from residues that act by themselves as intrinsic fluors, i.e., tryptophan, tyrosine and phenylalanine. As such, the fluorescent proteins of the subject invention are fluorescent proteins whose fluorescence arises from some structure in the protein that is other than the above specified single residues, e.g., it arises from an interaction of two or more residues.

In many embodiments, the polypeptides encoded by the subject nucleic acids are mutants of naturally occurring proteins, often proteins that occur in *Cnidarian* species, e.g., *Anthozoan* species. In certain embodiments, the nucleic acids are further characterized in that they encode non-aggregating mutants of wild type proteins (or mutants thereof) that are either from: (1) non-bioluminescent species, often non-bioluminescent *Cnidarian* species, e.g., non-bioluminescent *Anthozoan* species; or (2) from *Anthozoan* species that are not *Pennatulacean* species, i.e., that are not sea pens. As such, the nucleic acids of these embodiments may encode non-aggregating mutants of proteins from bioluminescent *Anthozoan* species, so long as these species are not *Pennatulacean* species, e.g., that are not *Renillan* or *Ptilosarcan* species. Of particular interest in certain embodiments are non-aggregating mutants of the the following specific wild type proteins (or mutants thereof): (1) amFP485, cFP484, zFP506, zFP540, drFP585, dsFP484, asFP600, dgFP512, dmFP592, as disclosed in application Ser. No. 10/006,922, the disclosure of which is herein incorporated by reference; (2) hcFP640, as disclosed in application Ser. No. 09/976,673, the disclosure of which is herein incorporated by reference; (3) CgCP, as disclosed in application Ser. No. 60/255,533, the disclosure of which is herein incorporated by reference; and (4) hcriGFP, zoanRFP, scubGFP1, scubGFP2, rfloRFP, rfloGFP, mcavRFP, mcavGFP, cgigGFP, afraGFP, rfloGFP2, mcavGFP2, mannFP, as disclosed in application Ser. No. 60/332,980, the dislcosure of which is herein incorporated by reference. Specific non-aggregating fluorescent polypeptides of interest include, but are not limited to: FP1-NA; FP3-NA; FP4-NA; FP6-NA; E5-NA; 6/9Q-NA; 7A-NA; mutM35-5 dimer-NA; and the like, where these particular non-aggregating mutants are further described infra.

In some embodiments, the subject nucleic acids encode a polypeptide that, in addition to the above characteristics, exhibits an increased isoelectric point (pI) relative to a reference protein, e.g., a corresponding wild type protein. Isoelectric point can be determined using any method known in the art. In some embodiments, the pI is a theoretical pI, calculated as described in the Examples. In some embodiments, a mutant protein of the invention has a pI in the range of from about 5.50 to about 7.00, from about 5.75 to about 6.75, from about 6.00 to about 6.50, or from about 6.10 to about 6.40.

Fluorescence brightness of a particular fluorescent protein is determined by its quantum yield multiplied by maximal extinction coefficient. Brightness of a chromoprotein may be expressed by its maximal extinction coefficient. In some embodiments, the subject nucleic acids encoded polypeptides show substantially the same or greater brightness in a cell than a reference protein, e.g., compared to the corresponding wild type protein, e.g., a mutant may be at least about 10%, at least about 20%, at least about 30%, at least about 40%, at least about 50%, at least about 60%, at least about 70%, at least about 80%, at least about 90%, at least about 100% (or two-fold), at least about 150%, at least about three-fold, or at least about four-fold, or more, brighter in a cell than the reference protein. A "cell" can be a prokaryotic cell or a eukaryotic cell. Methods of measuring brightness are known in the art. Brightness can be measured using any known method, including, but not limited to, visual screening, spectrophotometry, spectrofluorometry, fluorescent microscopy, by fluorescence activated cell sorting (FACS) machines, etc. In some instances, brightness of a subject mutant protein in a cell can be visually compared to the brightness of a reference protein in a cell of the same cell type, or another cell of the same cell line.

By nucleic acid composition is meant a composition comprising a sequence of DNA having an open reading frame that encodes a non-aggregating chromo/fluoro polypeptide of the subject invention, i.e., a chromo/fluoroprotein coding sequence, and is capable, under appropriate conditions, of being expressed as a non-aggregating chromo/fluoro protein according to the subject invention. Also encompassed in this term are nucleic acids that are homologous, substantially similar or identical to the nucleic acids of the present invention. Thus, the subject invention provides coding sequences encoding the proteins of the subject invention, as well as homologs thereof.

In addition to the above described specific nucleic acid compositions, also of interest are homologues of the above sequences. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). Of particular interest in certain embodiments are nucleic acids of substantially the same length as the nucleic acid identified as SEQ ID NOS: 13; 14; 15; 17; 19; 21; and 23, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e. the same as) or identical to the sequences of SEQ ID NOS: 14; 15; 17; 19; 21; and 23. By substantially similar is meant that sequence identity will generally be at least about 60%, usually at least about 75% and often at least about 80, 85, 90, or even 95%.

Also provided are nucleic acids that encode the proteins encoded by the above described nucleic acids, but differ in sequence from the above described nucleic acids due to the degeneracy of the genetic code.

Also provided are nucleic acids that hybridize to the above described nucleic acids under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the non-aggregating proteins of the invention are also provided. Mutant nucleic acids can be generated by random mutagenesis or targeted mutagenesis, using well-known techniques which are routine in the art. In some embodiments, chromo- or fluorescent proteins encoded by nucleic acids encoding homologues or mutants have the same fluorescent properties as the wild-type fluorescent protein. In other embodiments, homologue or mutant nucleic acids encode chromo- or fluorescent proteins with altered spectral properties, as described in more detail herein.

The subject nucleic acids may be present in an appropriate vector for extrachromosomal maintenance or for integration into a host genome, as described in greater detail below.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject polynucleotides and constructs thereof are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, a protein of interest (i.e., a protein being studied), etc. Fusion proteins may comprise a subject polypeptide, or fragment thereof, and a non-non-aggregating polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject non-aggregating protein portion of the fusion protein, and in certain embodiments not an *Cnidarian* protein or derivative/fragment thereof, i.e., it is not found in *Cnidarian* species.

Also provided are constructs comprising the subject nucleic acids inserted into a vector, where such constructs may be used for a number of different applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 2.5 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus Oocytes*, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21–25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163;

Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154: 737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci. (USA)* (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

The subject nucleic acids may be mutated in various ways known in the art to generate targeted changes in the sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated nucleic acid derivatives may be used to study structure-function relationships of a particular chromo/fluorescent protein, or to alter properties of the protein that affect its function or regulation.

Also of interest are humanized versions of the subject nucleic acids. As used herein, the term "humanized" refers to changes made to the nucleic acid sequence to optimize the codons for expression of the protein in human cells (Yang et al., *Nucleic Acids Research* 24 (1996), 4592–4593). See also U.S. Pat. No. 5,795,737 which describes humanization of proteins, the disclosure of which is herein incorporated by reference.

Protein/Polypeptide Compositions

Also provided by the subject invention are non-aggregating chromo- and/or fluorescent proteins and mutants thereof encoded by the subject nucleic acids, as well as polypeptide compositions related thereto. The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below.

In many embodiments, the subject proteins have an absorbance maximum ranging from about 300 to 700, usually from about 350 to 650 and more usually from about 400 to 600 nm. Where the subject proteins are fluorescent proteins, by which is meant that they can be excited at one wavelength of light following which they will emit light at another wavelength, the excitation spectra of the subject proteins typically ranges from about 300 to 700, usually from about 350 to 650 and more usually from about 400 to 600 nm while the emission spectra of the subject proteins typically ranges from about 400 to 800, usually from about 425 to 775 and more usually from about 450 to 750 nm. The subject proteins generally have a maximum extinction coefficient that ranges from about 10,000 to 50,000 and usually from about 15,000 to 45,000. The subject proteins typically range in length from about 150 to 300 and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the chromoproteins and their fluorescent mutants can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of a chromoproteins may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest are non-aggregating mutant polypeptides or variants of chromo/fluoroproteins (and mutants thereof) from the following specific Anthozoan species: *Anemonia majano, Clavularia* sp., *Zoanthus* sp., *Zoanthus* sp., *Discosoma striata, Discosoma* sp. "red", *Anemonia sulcata, Discosoma* sp "green", *Discosoma* sp. "magenta." Specific non-aggregating fluorescent polypeptides of interest include, but are not limited to: FP1-NA; FP3-NA; FP4-NA; FP6-NA; E5-NA; 6/9Q-NA; 7A-NA; and the like.

Homologs or proteins (or fragments thereof) that vary in sequence from the amino acid sequences of the above provided specific non-aggregating polypeptides are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151–153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the sequences of the above provided specific proteins, where by substantially identical is meant that the protein has an amino acid sequence identity to the one of the above specifically provided proteins of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins which are mutants of the above specifically described proteins are also provided. Mutants may retain biological properties of the wild-type (e.g., naturally occurring) proteins, or may have biological properties which differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. victoria*), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Mutants of the above specifically provided proteins are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides may be synthetically produced using any convenient protocol, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject non-aggregating fluorescent proteins. Suitable antibodies are obtained by immunizing a host animal with peptides comprising all or a portion of the subject protein. Suitable host animals include mouse, rat sheep, goat, hamster, rabbit, etc. The immunogen may comprise the complete protein, or fragments and derivatives thereof.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) J.B.C. 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) P.N.A.S. 84:3439 and (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) Mol. Cell. Bio. 3:280), Rous sarcoma virus LTR (Gorman et al. (1982) P.N.A.S. 79:6777), and moloney murine leukemia virus LTR (Grosschedl et al. (1985) Cell 41:885); native Ig promoters, etc.

Transgenics

The subject nucleic acids can be used to generate transgenic, non-human plants or animals or site specific gene modifications in cell lines. Transgenic cells of the subject invention include one or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), Meth. Enzymol. 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct.

Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275–295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is Agrobacterium mediated transformation. With Agrobacterium mediated transformation, co-integrative or binary vectors comprising the exogenous DNA are prepared and then introduced into an appropriate Agrobacterium strain, e.g. A. tumefaciens. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject non-aggregating chromoproteins and fluorescent mutants thereof find use in a variety of different applications, where the applications necessarily differ depending on whether the protein is a chromoprotein or a fluorescent protein. Representative uses for each of these types of proteins will be described below, where the following described uses are merely representative and are in no way meant to limit the use of the subject proteins to those described below.

Chromoproteins

The subject chromoproteins of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins may be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent proteins of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969–973, a green fluorescent protein from *Aequoria Victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

Another application in which the subject fluorescent proteins find use is BRET (Bioluminescence Resonance Energy Transfer). BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci.* USA 96:151–156. BRET assays may be performed by genetically fusing a bioluminescent donor protein and a fluorescent acceptor protein independently to two different biological partners to make partner A-bioluminescent donor and partner B-fluorescent acceptor fusions. Changes in the interaction between the partner portions of the fusion proteins, modulated, e.g., by ligands or test compounds, can be monitored by a change in the ratio of light emitted by the bioluminescent and fluorescent portions of the fusion proteins. In this application, the subject proteins serve as donor and/or acceptor proteins. BRET assays can be used in many of the assays as FRET, which assays are noted above.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1–3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH 6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1–2 min and reaches a steady state level after 5–10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throuhgput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidyl-inositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like.

The subject non-aggregating fluorescent proteins of the subject invention may also be used in cell labeling applications, as described in U.S. Application Ser. No. 60/261,448; the disclosure of which is herein incorporated by reference. For example, a fusion protein comprising a non-aggregating protein of the invention and a member of a specific binding partner that binds to a cell-surface molecule (e.g., a ligand that binds to to a cell surface receptor; an antibody the binds to a cell surface protein; a counterreceptor that binds to a cell surface protein; and the like) can be used to identify and/or fractionate and/or isolate one or more cell populations from a mixture of cells. In some embodiments, the fusion proteins multimerize, and, in some of these embodiments, cell labeling applications take advantage of the multimerization feature. Thus, in some embodiments, the invention provides intrinsically fluorescent multimeric, non-aggregating fusion protein complex comprising a polypeptide of the present invention, and methods for use of the fusion protein complex in cell labeling methods.

In one non-limiting example, a fusion protein comprising an antigen-binding portion of an MHC molecule, and a polypeptide of the invention can be generated, using standard molecular biology techniques. Such fusion proteins would be expected to multimerize, but not aggregate. The multimerization property of the non-aggregating component of the fusion protein would serve to bring together the MHC portion of the fusion protein, forming multimeric fusion protein complexes, and the multimeric fusion protein complex could be charged with a peptide antigen. Such fusion proteins charged with a peptide antigen could be used to identify T lymphocytes that bear on their surface a T cell receptor specific for the same peptide antigen. Because the peptide antigens and MHC peptide-presenting domains of the fusion protein complexes can both be varied, the intrinsically fluorescent multimeric complexes can be used, in general, fluorescently to label a nearly infinite variety of T lymphocytes based upon the antigen (and MHC) specificity of their antigen receptors.

It is, therefore, another aspect of the present invention to provide methods for using a protein of the present invention detectably to label (stain) T lymphocytes based upon the specificity of their antigen receptors.

In a first embodiment, the method comprises contacting a T lymphocyte to be labeled with an intrinsically fluorescent multimeric, non-aggregating fusion protein complex comprising a polypeptide of the present invention, the complex having peptide antigen and MHC peptide-presenting domains for which the antigen receptor of the T lymphocyte is specific, for a time and under conditions sufficient to permit detectable binding of the complex to the T lymphocyte.

In the present context, a T lymphocyte is said to be specific for a peptide antigen when the affinity of its antigen receptor (TCR) for the peptide antigen in the MHC context of the complex is sufficiently high as to confer upon the complex as a whole avidity for the T lymphocyte sufficient to achieve detectable binding of the complex to TCRs on the lymphocyte surface.

By this definition, it is not impossible for a single T lymphocyte, having a single or TCR species on its surface, to be said to be specific for a plurality of (typically closely related) peptide antigens. In such cases, the TCR will typically have greater affinity for one of the peptides than for the others. Often, the peptide antigen(s) for which the T lymphocyte is said to be specific by this definition will also be capable of stimulating cytokine expression by the T lymphocyte; such a functional response is not, however, required, since the utility of the multimeric complexes of the present invention, as for MHC tetramers, is not limited to labeling and identification of functionally responsive T lymphocytes.

Conditions and times adequate for such labeling can conveniently be adapted from those used in the art for staining T lymphocytes with MHC tetramers or MHC/Ig fusions.

For example, Altman et al., *Science* 274:94–96 (1996) stain 200,000 cytotoxic lymphocytes with MHC tetramers by incubation at 4° C. for one hour at a concentration of tetramer of approximately 0.5 mg/ml; the NIAID Tetramer facility (available on the world wide web at www.niaid.nih.gov/reposit/tetramer/genguide.htm) presently recommends staining at each of 4° C., room temperature, and 37°, for 15–60 minutes, to optimize signal to noise ratio, with decreasing incubation times used for higher temperatures. Greten et al., *Proc. Natl. Acad. Sci. USA* 95:7568–7573 (1998) stain $1\times10^6$ peripheral blood mononuclear cells at 4° with 3 μg of MHC class I MHC/Ig chimera.

Thus, T lymphocytes can conveniently be labeled with the intrinsically fluorescent multimeric complexes in the methods of the present invention using at least about 0.1 μg, typically at least about 0.25 μg, more typically at least about 1 μg, 2 μg, 3 μg, 4 μg, or even at least about 5 μg of multimer to label about $10^4$, $10^5$, $10^6$ or even $10^7$ peripheral blood mononuclear cells using an incubation of 15–60 minutes at a temperature between 4° C. and 37° C.

Starting with these broad, exemplary, guidelines, those skilled in labeling T lymphocytes using MHC tetramers, MHC/Ig fusions, and fluorophore-conjugated antibodies will readily be able to determine optimal labeling conditions. Variables that affect the amount of multimeric reagent to be used and the temperature and duration of staining include those related to the T lymphocytes—the number of T lymphocytes in the sample that are specific for the peptide antigen (and MHC) of the complex, the total number of cells in the sample, the form of the cellular sample (e.g., whole blood, whole blood after red blood cell lysis, Ficoll-purified peripheral blood mononuclear cell (PBMC) fraction)—and those related to the multimeric complex, including the stoichiometry and molecular weight of the labeling complex, the identity of the peptide antigen, and the choice of MHC alleles included in the complex.

To optimize labeling conditions, labeling reactions can readily be performed using parallel aliquots of the cellular sample to be labeled using a single species of multimeric complex and varying labeling conditions (e.g., temperature, duration, complex concentration, cell number, cell concentration, cellular purity). Negative controls can include labeling reactions using no multimer, using multimer lacking peptide, and/or using multimer containing MHC peptide-presenting domains and/or peptide antigen that will not be recognized by T lymphocytes in the cellular sample. Effectiveness of labeling can be readily determined for each aliquot by flow cytometric enumeration of T lymphocytes in the sample that bind the fluorescent complex. As is well known in the flow cytometric arts, the labeled cells can be washed prior to flow cytometry to remove unbound complex from the cells and medium. All of these techniques and approaches are routine, and routinely performed by technicians, in the flow cytometric arts.

Typically, the T lymphocytes to be labeled are present within a heterogeneous sample of cells, and the goal of labeling is to detect, and often to enumerate, the antigen specific T lymphocytes within this population.

Thus, in another aspect, the present invention provides methods for detecting, in a sample of cells, T lymphocytes that are specific for a chosen antigen. The method comprises contacting the sample with an intrinsically fluorescent multimeric complex according to the present invention, wherein the peptide antigen of the complex is the chosen antigen and the MHC presenting domains of the complex are those for which the T lymphocytes desired to be detected will be restricted, for a time and under conditions sufficient to permit detectable binding of the complex to T lymphocytes in the sample that are specific for the chosen antigen and MHC; and then detecting specific T lymphocytes in the sample by the fluorescence of the complex bound thereto.

The detection of cell-bound fluorescence is typically performed using a flow cytometer, such as a FACSVANTAGE™, FACSVANTAGE™ SE, or FACSCALIBUR™ flow cytometer (Becton Dickinson Immunocytometry Systems, San Jose, Calif., USA). The lasers chosen for excitation will be determined by the absorption spectrum of the multimeric complex and of any additional fluorophores desired to be detected concurrently in the sample. For example, if the multimeric complex has the spectral characteristics of native DsRed—e.g., a homotetramer in which the fusion protein subunits all have the native DsRed GFP-like chromophore—a standard argon ion laser with 488 nm line can be used for excitation. For detection, the filter sets and detector types will be chosen according to the emission spectrum of the multimeric complex and of any additional fluorophores desired to be detected in the sample. For example, if the multimeric complex has the spectral characteristics of native DsRed, with emission maximum at about 583 nm, fluorescence emission from the complex can be detected in the FL2 channel using a PE setup.

Alternatively, cell-bound complex fluorescence can be detected using a microvolume fluorimeter, such as the IMAGN 2000 (Becton Dickinson Immunocytometry Systems, San Jose, Calif., USA). Applications of microvolume fluorimetry to, and conditions for, characterization of blood cell are described, inter alia, in Seghatchian et al., *Transfus.*
*Sci.* 22(1–2):77–9 (2000); Glencross et al., *Clin. Lab. Haematol.* 21(6):391–5 (1999); and Read et al., *J. Hematother.* 6(4):291–301 (1997).

Alternatively, cell-bound complex fluorescence can be detected using a laser scanning cytometer (Compucyte Corp., Cambridge, Mass., USA).

Cell-bound fluorescence of the multimeric complex can also be detected directly on a microscope slide, whether from touch prep, cytospin prep, or tissue sample, using conditions essentially as described in Skinner et al., "Cutting edge: In situ tetramer staining of antigen-specific T cells in tissues," *J. Immunol.* 165(2):613–7 (2000).

The T lymphocyte-containing sample can be a whole blood sample, typically a peripheral venous blood specimen drawn directly into an anticoagulant collection tube (e.g., EDTA-containing or heparin-containing VACUTAINER™ tube, Becton Dickinson VACUTAINER™ Systems, Franklin Lakes, N.J., USA).

Advantageously, the T lymphocyte-containing sample can also be a whole blood sample that has been treated before detection with a red blood cell (RBC) lysing agent as is described, inter alia, in Chang et al., U.S. Pat. Nos. 4,902,613 and 4,654,312; lysing agents are well known in the art and are available commercially from a number of vendors (FACS™ Solution, Becton Dickinson Immunocytometry Systems, San Jose, Calif., USA; CAL-LYSE™ Lysing Solution, Caltag Labs, Burlingame, Calif., USA; No-Wash Lysing Solution, Beckman Coulter, Inc., Fullerton, Calif.). The sample can optionally be washed after RBC lysis and before detection.

The sample within which T lymphocytes are desired to be detected according to the methods of the present invention can also be a peripheral blood fraction, advantageously a mononuclear cell (PBMC) fraction. PBMCs can be prepared according to any of the well-known art-accepted techniques, including centrifugation through Ficoll-Paque (Amersham Pharmacia Biotech, Piscataway, N.J., USA) and centrifugation directly in a cell preparation blood collection tube (VACUTAINER™ CPT™ Cell Preparation Tube, Becton Dickinson, Franklin Lakes, N.J., USA).

The sample can also advantageously be a sample enriched in T lymphocytes, e.g. cultured lymphocytes (as from a clonal cell line or multiclonal culture), lymphocytes extracted or eluted from a tissue with lymphocytic infiltrate (e.g., tumor infiltrating lymphocytes extracted from a tumor biopsy and optionally expanded in culture), lymphocytes drawn from lymphatics or thymus, or lymphocytes obtained after a first round of fluorescence-activated cell sorting.

In another embodiment, the method further comprises enumerating the antigen-specific T lymphocytes so detected. Enumeration can conveniently be expressed in the form of a total cell count, percentage of antigen-specific T lymphocytes among cells assayed (either total, mononuclear, or T lymphocytic), or percentage of antigen-specific lymphocytes in a T cell subset.

For several of these metrics, it is necessary additionally to quantitate the total number of T lymphocytes within the sample as a whole, or the total number of T lymphocytes of a particular subset within the sample as a whole.

Thus, in other embodiments, the method of the present invention further comprises contacting the sample with at least one fluorophore-conjugated antibody, the antibody selected from the group consisting of pan-T antibodies and T cell subsetting antibodies, and then detecting fluorescence concurrently from the multimeric fluorescent complex and from the fluorophore-conjugated antibodies.

Antibodies usefully used in this embodiment include antibodies specific for CD3, CD4, CD8, CD45RO, CD45RA, and CD27. As would be understood, the antibodies would typically be specific for the marker as expressed by the taxonomic species (human, mouse, rat, etc.) whose T lymphocytes are being detected, or would be cross-reactive therewith.

As is well known in the flow cytometric arts, the pan-T and/or T lymphocyte subsetting antibodies can be used for any or all of triggering data acquisition, live gating, or gating prior-acquired data.

It is often advantageous in the methods of the present invention to acquire a large number of events since, in many samples, antigen-specific T lymphocytes occur infrequently. In addition, it is possible at times to improve the signal to noise ratio for detecting antigen-specific T lymphocytes by triggering or gating on fluorescence from antibodies specific for T lymphocyte activation antigens.

Thus, in another embodiment, the method further comprises contacting the sample with at least one fluorophore-conjugated antibody specific for a T cell activation antigen, and then detecting fluorescence concurrently from the multimeric fluorescent complex and from the fluorophore-conjugated antibodies. The antibodies can usefully be specific for an activation antigen selected from the group consisting of CD69, CD25, CD71 and MHC class II (for labeling human T lymphocytes, HLA-DR).

Advantageously, the antibodies used in the methods of the present invention will be prior-conjugated directly to a fluorophore, typically a fluorophore whose emission is flow cytometrically distinguishable from that of the intrinsically fluorescent multimeric T cell labeling complex and from that of other fluorophores concurrently used in the method. Fluorophores can usefully be selected from the group consisting of fluorescein isothiocyanate (FITC), phycoerythrin (PE), peridinin chlorophyll protein (PerCP), allophycocyanin (APC), Texas Red, ALEXA FLUOR® 488 (Molecular Probes, Inc., Eugene Or.), and the tandem fluorophores PerCP-Cy5.5, PE-Cy5, PE-Cy7, and APC-Cy7. Antibodies can also usefully be conjugated to biotin, permitting second stage detection using fluorophore-labeled streptavidin.

The methods of the present invention for detecting and enumerating antigen-specific T lymphocytes can be used for the same purposes as are prior art methods, including use of MHC tetramers and MHC/Ig chimeras, as well as other functional assays, such as limiting dilution assay, ELISPOT, and flow cytometric detection of intracellular cytokine expression (Waldrop et al., *J. Clin. Invest.* 99(7):1739–50 (1997)). The methods can thus be used, e.g., to assess CD4$^+$ and CD8$^+$ T cell responses to infection, to vaccines, and in autoimmunity.

Depending upon the instrument used, detection of antigen-specific T lymphocytes can be coupled directly or indirectly to their sorting, thus providing, in other aspects of the invention, methods for enriching and for depleting a sample for T lymphocytes that are specific for a chosen antigen.

In general, the method comprises contacting the sample with an intrinsically fluorescent multimeric complex of the present invention, wherein the peptide antigen of the complex is the chosen antigen and the MHC presenting domains of the complex are those for which the T lymphocytes desired to be enriched or depleted will be restricted, for a time and under conditions sufficient to permit detectable binding of the complex to T lymphocytes in the sample that are specific for the chosen antigen and MHC. After binding, labeled T lymphocytes are enriched or depleted based upon the fluorescence of the complex bound thereto.

Such methods are conveniently performed using a fluorescence activated cell sorter: sorting based at least in part upon fluorescence from the multimeric complex of the present invention directly depletes the sample from which the cells are removed and enriches the aliquot into which the cells are placed.

It is possible, however, to use the multimers of the present invention to enrich or deplete cells using approaches other than fluorescence-activated cell sorting.

For example, T lymphocytes stained specifically with the multimer can be separated magnetically, rather than fluorimetrically, by further conjugation of the TCR-bound complex to a superparamagnetic particle. This can be done, e.g., using an antibody specific for an epitope of the fusion protein (e.g., where DsRed contributes GFP-like chromophore and/or multimerization domains, the antibody can be the DsRed-specific antibody available commercially from Clontech Labs, Palo Alto, Calif., USA).

As another example, T lymphocytes stained specifically with the multimer can be separated using biotin/avidin affinity interactions, rather than fluorescence, by further conjugation of the TCR-bound complex to biotin, followed by use of an avidin affinity matrix. This further labeling of the multimeric complex can be done indirectly using a biotin-conjugated antibody specific for an epitope of the fusion protein. Alternatively, the multimer can itself be prior-conjugated to biotin, either chemically or, upon engineering of a BirA substrate peptide into the complex (typically the fusion protein), enzymatically.

Samples enriched in antigen-specific T cells according to the methods of the present invention can be used in vitro for study of specific interactions of antigen-specific T cells with antigen-presenting cells, cytotoxic targets, B cells, or other cellular elements of the immune system. Samples enriched in antigen-specific T cells according to the method of the present invention can also be used in vitro to modify such interactions. See, e.g., Dal Porto et al., et al., *Proc. Natl. Acad. Sci. USA* 90:6671–6675 (1993).

Samples enriched in antigen-specific T cells according to the methods of the present invention can also be used for in vivo therapeutic intervention, such as for tumor immunotherapy. See, e.g., Oelke et al., *Clin. Cancer Res.* 6(5): 1997–2005 (2000).

The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Sequences of Parental Aggregating Wild-Type *Anthozoan* Proteins and Mutants Thereof The following table summarizes the properties of nine specific wild type *Anthozoan* proteins of the subject invention:

TABLE I

| NFP | Species | Identifier | FIG. | Amino Acid Sequence ID No. | Nucleotide Sequence ID No. |
|---|---|---|---|---|---|
| 1 | *Anemonia majano* | amFP486 | 1 | 02 | 01 |
| 3 | *Zoanthus* sp. | zFP506 | 2 | 04 | 03 |
| 4 | *Zoanthus* sp. | zFP538 | 3 | 06 | 05 |
| 6 | *Discosoma* sp. "red" | drFP583 | 4 | 08 | 07 |
| 7 | *Anemonia sulcata* | asFP600 | 5 | 10 | 09 |
| 8 | 6/9Q | drFP583/dmFP592 | 6 | 12 | 11 |

II. Mutagenesis

Site-directed mutagenesis was performed by PCR with primers containing appropriate target substitutions. All mutants were cloned between BamHI and HindIII restriction sites of the pQE30 vector (Qiagen). Recombinant proteins were 6× Histidine-tagged to contain the sequence 'MRHHHHHHGS' (SEQ ID NO: 31) instead of the first Met. After overnight expression in *E. coli*, fluorescent proteins were purified using TALON™ Metal Affinity Resin (CLONTECH). SDS-PAGE analyses revealed that proteins were at least 95% pure.

In greater detail, mutagenesis was performed by the overlap extension method (Ho, S. N., Hunt, H. D., Horton, R. M., Pullen, J. K., Pease, L. R. Site-directed mutagenesis by overlap extension using the polymerase chain reaction. (Gene 1989, 77, 51–59). Briefly, two overlapping fragments of FP coding region were amplified. "Forward cloning" and "reverse mutagenesis" primers were used for 5'-end fragment amplification, and "forward mutagenesis" and "reverse cloning" primers were used for 3'-end fragment amplification. PCR was carried out using ADVANTAGE® 2 Polymerase Mix (CLONTECH) in 1× manufacturer's buffer supplemented with 100 µM of each dNTP, 0.2 µM of each primer and 1 ng of plasmid DNA in 25 µl (final volume). The cycling parameters were set at: 95° C. for 10 seconds, 65° C. for 30 s, 72° C. for 30 s. 20 cycles were completed using PTC-200 MJ Research thermocycler. To remove plasmids encoding initial (wild type) protein, the 5'- and 3'-fragments were excised from 2% low-melting agarose gel in 1×TAE buffer. To drain the DNA solution, the gel pieces were subjected to 3 freeze-thaw cycles. 5'- and 3'-fragments were combined to obtain full-length cDNA as follows. Equal volumes of 5'-fragment solution, 3'-fragment solution and 3×PCR mixture containing ADVANTAGE® 2 Polymerase Mix, buffer and dNTPs were mixed together and subjected to 2–3 cycles of 95° C. for 20 s, 65° C. for 30 min, 72° C. for 30 s. Then, the reaction was diluted 10 fold and 1 µl of the diluted sample was used as a template for PCR with forward and reverse cloning primers (as described above for 5'- and 3'-fragments amplification). As a result, ready-for-cloning fragments containing full-length coding regions with target substitution(s) were generated.

Mutant cDNAs were digested with BamHI and HindIII (the cloning primers contain sites for these endonucleases), and then cloned into pQE30 (Qiagen) digested with BamHI and HindIII. Recombinant proteins contained 6×His tag on the N-terminus.

Selected *E. coli* clones were grown at 37° C. in 50 ml to an optical density of (OD) 0.6. At that point, the expression of recombinant FP was induced with 0.2 mM IPTG. The cultures were then incubated overnight. The following day, cells were harvested by centrifugation, resuspended in buffer (20 mM TRIS® HCL, (hydroxymethyl aminomethane hydroxychlride, pH 8.0; 100 mM NaCl), and disrupted by sonication. Fluorescent proteins were purified from the soluble fraction using TALON™ Metal Affinity Resin (CLONTECH). Proteins were at least 95% pure according to SDS-PAGE.

III. Mutants Generated

TABLE 2 provides Details Regarding representative Non-Aggregating Mutants Generated Using the Above Protocol

| Non-Aggregating Mutant Designator | Wild type protein | Parental mutant | Differences between wild-type protein and parental mutant | Target substitutions in non-aggregating mutant | FIG. Seq ID NOs |
|---|---|---|---|---|---|
| NFP6-NA E57-NA DsRED2 | drFP583 | "E57" (V105A, I161T, S197A) | Faster and more complete folding in *E. coli* | R2A, K5E, K9T | FIG. 7 SEQ ID NO. 13 |
| E5-NA Timer-NA | drFP583 | "Timer" (V105A, S197T) | Change color with time | R2A, K5E, K9T | FIG. 8 Seq ID NO: 14 |
| 6/9Q-NA | dsFP593/ drFP583 | ds/drFP616 | Red-shifted fluorescence | S2del, C3del, K5E, K9T | |

TABLE 2-continued provides Details Regarding representative Non-Aggregating Mutants
Generated Using the Above Protocol

| Non-Aggregating Mutant Designator | Wild type protein | Parental mutant | Differences between wild-type protein and parental mutant | Target substitutions in non-aggregating mutant | FIG. Seq ID NOs |
|---|---|---|---|---|---|
| NFP3-NA | zFP506 | N66M | 1.8-fold increase in brightness in E. coli | K5E, K10E | FIG. 9 SEQ ID NOs: 15 & 16 |
| NFP4-NA | zFP538 | M129V | More complete folding in E. coli | K5E, K9T | FIG. 10 SEQ ID NOs: 17 & 18 |
| NFP1-NA | amFP486 | K68M | 1.5-fold increase in brightness in E. coli | K6E | FIG. 11 SEQ ID NOs: 19 & 20 |
| NFP7-NA M35-5NA | asFP595 | "M35-5" (F4L, K12R, F35L, T68A, F84L, A143S, K163E, M202L) | 5-fold increase in brightness in E. coli, in comparison with mutant T68A, A143S [3] | K6T, K7E | FIG. 12 SEQ ID NOS: 21 & 22 |
| NFP7-NA dimer M35-5 dimer-NA | asFP595 | "M35-5" (F4L, K12R, F35L, T68A, F84L, A143S, K163E, M202L) | | K6T, K7E | FIG. 13 SEQ ID NOS: 23 & 24 |

Figure 14:
FIG. 14. Multiple alignment of N-terminal regions of the fluorescent proteins. The arrow above the sequences represents the first β-sheet in the proteins, based on GFP and drFP583 structures. Amino acid residues substituted in the non-aggregating mutants are shaded.

FIG. 14 provides an alignment of certain non-aggregating mutants as described above.

IV. Characterization of Representative Non-Aggregating Mutants

A. Materials and Methods

Theoretical pI

Theoretical pI were calculated using ProtParam program available on Web site which is produced by putinng: "http://" before and ".html" after "expasy.pku.edu.cn/tools/protoparam" and described in Appel R. D., Bairoch A., Hochstrasser D. F. A new generation of information retrieval tools for biologists: the example of the ExPASy WWW server. *Trends Biochem. Sci.* 1994, 19:258–260.

Methods of Evaluating Protein Aggregation

1. "Pseudo-native" protein electrophoresis. For fast evaluation of aggregation properties of the mutant proteins we used a simple method which we term "pseudo-native" protein electrophoresis. This method is based on applying on a common sodium dodecyl sulfate-polyacrylamide gel (SDS-PAG) the non-boiled protein samples. In these conditions, FPs remain fluorescent. In addition, these conditions maintain the super-molecular structure of applied proteins. High-molecular weight aggregated proteins remain at the top of the gel, while tetramer proteins migrate as a band >100 kD.

2. Light scattering. This method is based on light scattering in solution by particles of aggregated protein. The larger size and amount of such particles, the greater the light scattering. As light scattering depends on the wavelength of light (scattering is much more pronounced for short waves), the aggregation results in general slope of absorption spectrum. In general, it is preferable to evaluate aggregation by the ratio of absorption at a shorter wavelength (where absorption of non-aggregated protein is minimal) to absorption at a longer wavelength (where absorption of non-aggregated protein is maximal). For instance, for E57 one might evaluate aggregation by measuring the ratio of absorption as follows: absorption (400 nm)/absorption (566 nm). In a non-aggregated protein sample, this ratio should be close to zero.

The mutants were tested under the same buffer conditions, which conditions do not prevent aggregation, at concentrations of 1 mg/ml.

3. Brightness in mammalian cell line. Particular mutants were transiently transfected into the mammalian cell line Phoenix using Cl vector (CLONTECH). Aggregation was evaluated by visual inspection of the number of cells expressing FP using fluorescent microscope.

4.

Exact kinetics of aggregation in vivo is unclear because it is difficult to measure this process within living cells. Probably, aggregation depends on FP concentration since brighter cells usually display more pronounced FP aggregates. Nevertheless, aggregation picture can be observed even in low fluorescent cells as soon as the signal become visible. This indicates that threshold value of FP concentration sufficient for aggregation is rather low.

Aggregation of purified FPs is additionally observed in vitro. For example, almost all Anthozoa FPs partially precipitate from solution (PBS) without any loss of color or fluorescence. To visualize aggregation of purified FPs, we used "pseudo-native" protein electrophoresis, based on the discontinuous SDS-PAGE of non-heated protein samples (Baird, G. S., Zacharias, D. A. and Tsien, R. Y. (2000) Proc. Natl. Acad. Sci. U.S.A. 97, 11984–11989). Under these conditions, FPs retain not only fluorescent properties, but also super-molecular structure: high-molecular weight-aggregated proteins remain at the top of the gel, while oligomers migrate as bands of the high molecular weights.

B. Results

Red fluorescent drFP583 was the first protein subjected to mutagenesis. An improved mutant of DsRed (the commercially available version of drFP583 with altered codon usage optimized for expression in mammalian cells), designated E57, was used as a parental gene (Table 2). Mutants of E57 containing the substitutions R2A, K5E, K9T (in different combinations) were generated. After expression in *E. coli* and purification, these proteins were analyzed by pseudo-native PAGE (see above). All mutants displayed lower levels of aggregation in comparison with parental E57, and the R2A substitution appeared to have the strongest impact on this outcome (not shown). A mutant, denoted E57-NA, containing all three substitutions (R2A, K5E, and K9T) that showed no aggregation (FIG. 15) and was very similar to E57 in terms of excitation-emission maxima, fluorescence brightness and maturation speed, was selected as the optimal protein.

E57-NA displayed an excellent fluorescence image in mammalian cells (FIG. 16). In most cells, nuclei and nucleoli were clearly visible, and cell borders and processes were well-defined. In contrast, the fluorescence of E57-expressing cells was smeared, with no visible intracellular structures. The borders of the fluorescent signal often did not coincide with cell borders and processes, so that cells looked rounded. Therefore, both in vivo and in vitro tests confirmed that the E57-NA protein was low-aggregating. Importantly, pilot trials of E57-NA in other laboratories showed greatly decreased toxicity of this protein in comparison with both DsRed and E57, during expression in cell lines (B. Angres, Clontech, Palo-Alto, Calif., USA, personal communication), *Xenopus* embryos (A. Zaraisky, IBCh, Moscow, Russia, personal communication), and plants (A. Touraev, IMG, Vienna Biocenter, Vienna, Austria, personal communication). Now E57-NA is commercially available from Clontech as DsRed2.

Figure 15:
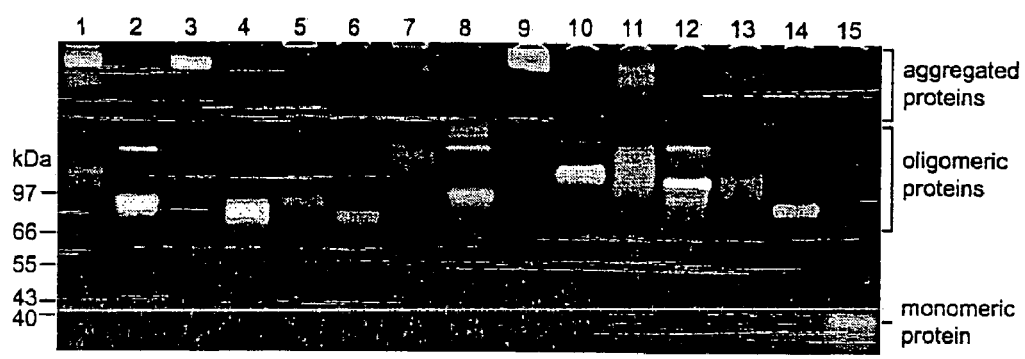
FIG. 15. Pseudo-native gel-electrophoresis of parental fluorescent proteins (odd lanes) and their non-aggregating mutants (even lanes). The photograph was taken under UV illumination. Aggregated proteins are observed in the stacking gel. Oligomeric proteins migrate through the separating gel as bands of high molecular weights (expected MW of FP monomers and tetramers are about 27 and 108 kDa). Molecular weight standards are shown on the left of the gel. Lanes: 1—DsRed mutant E57; 2—E57-NA; 3—DsRed mutant Timer; 4—Timer-NA; 5—ds/drFP616; 6—ds/drFP616-NA; 7—zFP506 mutant N66M; 8—zFP506-N66M-NA; 9—zFP538 mutant M129V; 10—zFP538-

Recently, an interesting mutant of DsRed entitled 'Timer', because it changes color with time, was described. To generate a non-aggregating version of this protein, we employed the three substitutions mentioned above. The novel mutant, Timer-NA, was generated (Table 2), which possessed practically the same maturation properties with color change as parental Timer, but did not form aggregates on pseudo-native PAGE (FIG. 15). In mammalian cells, the differences between Timer and Timer-NA were analogous to those between E57 and E57-NA (FIG. 16).

The next FP targeted was ds/drFP616 (6/9Q), which displays red-shifted fluorescence with a peak at 616 nm. The protein was generated by the shuffling of two red FPs (dsFP593 and drFP583), followed by random mutagenesis. However, ds/drFP616 showed extremely high aggregation. The mutation of two Lys residues at positions 5 and 9 at the N-terminal region of ds/drFP616 as for E57 and Timer (FIG. 14, Table 2), resulted in a significant decrease in the amount of aggregated protein on pseudo-native PAGE, although residual aggregation was still detected in the Lys mutant, ds/drFP616-K5E/K9T (not shown). After the screening of *E. coli* clones producing protein, one was selected that displayed complete absence of aggregation on pseudo-native PAGE (FIG. 15). Sequence analyses revealed that this clone contains two additional mutations in the N-terminal region of the protein (Ser-2 and Cys-3, deleted accidentally during cloning procedures). When expressed in eukaryotic cells, the mutant, designated ds/drFP616-NA (6/9QNA), showed significant improvement in fluorescence image, similar to E57-NA and Timer-NA. In contrast to the bright but completely unstructured blot-like image of parental ds/drFP616, ds/drFP616-NA was more evenly distributed in nuclei and cytoplasm (FIG. 16).

The mutagenesis strategy described above was subsequently applied to four FPs of different colors: green zFP506, yellow zFP538, red asFP595, and cyan amFP486 proteins, based on the improved mutants generated earlier by random mutagenesis (Table 2). When expressed in *E coli*, mutant proteins displayed greater brightness and faster and more complete protein folding, in comparison with corresponding wild-type proteins (unpublished data). However, the introduced substitutions had no influence on the aggregation properties of these FPs. In an attempt to decrease aggregation tendency, all lysines near the N-termini of the proteins were mutated (FIG. 14, Table 2). In vitro analyses of resulting secondary protein mutants confirmed no aggregation (FIG. 15). Additionally, all four non-aggregating mutants (zFP506-N66M-NA, zFP538-M129V-NA, amFP486-K68M-NA, and asFP595-M35-5-NA) displayed clear improvement in fluorescence images in mammalian cells, analogous to E57-NA, Timer-NA, and ds/drFP616-NA (FIG. 16, images for amFP486 and asFP595 are not shown).

C. Conclusion

In summary, we conclude that basic residues near the N-termini of Anthozoa FPs play a prominent role in the formation of protein aggregates. A number of examples of the significant effect of single amino acid substitutions on protein aggregation are documented. Similarly, substitution of one to three residues in FPs led to a considerable increase in protein solubility.

V. Additional Characterizations

TABLE 3

Properties of E57-based mutants with altered pI.

| N | Substitutions (compared with E57) See FIG. 4 | Theoretical pI | Visual brightness in *E. coli* | Aggregation in vitro (pseudonative PAGE)[a] | Aggregation in vitro (light in scattering test)[b] | Visual brightness in eukaryotic cell culture | Aggregation in eukaryotic cell culture |
|---|---|---|---|---|---|---|---|
| 1 | "E57" | 7.78 | high | High | 1 | high | high |
| 2 | Q137E, Q188E | 6.72 | high | Low | 0.05 | low | medium |
| 3 | R2del, Q137E, Q188E | 6.46 | high | Very low | 0.03 | medium | low |
| 4 | R2del, Q137E, Q188EI180A, M182K | 6.72 | high | High | NT | low | high |
| 5 | R2A, K5E, K9T | 6.08 | high | Very low | 0.025 | high | very low |
| 6 | R2del, R13S, R17E | 6.08 | high | Low | NT | low | low |
| 7 | T21D | 6.72 | medium | High | NT | NT | NT |
| 8 | R36D | 6.46 | high | Medium | NT | NT | NT |

TABLE 3-continued

Properties of E57-based mutants with altered pI.

| N | Substitutions (compared with E57) See FIG. 4 | Theoretical pI | Visual brightness in E. coli | Aggregation in vitro (pseudonative PAGE)[a] | Aggregation in vitro (light scattering test)[b] | Visual brightness in eukaryotic cell culture | Aggregation in eukaryotic cell culture |
|---|---|---|---|---|---|---|---|
| 9 | R2A, K5E, K9T, R13S, R17E | 5.65 | high | Very low | 0.02 | low | low |

[a]This method is based on applying on a SDS-PAGE the non-boiled protein samples. In these conditions FPs are fluorescent and the conditions of electrophoresis preserve super-molecular structure.
[b]Ratio: (Absorption (400 nm) - Absorption (650 nm)/(Absorption (566 nm) - Absorption (650 nm)).

It is evident from the above discussion and results that the subject invention provides important new mutant fluorescent proteins and nucleic acids encoding the same, where the subject mutants have improved features, i.e., non-aggregation, when compared with a reference chromo/fluoroprotein, and where the subject proteins and nucleic acids find use in a variety of different applications. As such, the subject invention represents a significant contribution to the art.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid present in other than its natural environment that encodes a non-aggregating chromo- or fluorescent mutant protein, wherein said nucleic acid has a sequence identity of at least 95% with SEQ ID NO:13.

2. The nucleic acid according to claim 1, wherein the chromo- or fluorescent mutant protein is from a non-bioluminescent *Cnidarian* species.

3. The nucleic acid according to claim 2, wherein said non-bioluminescent *Cnidarien* species is an *Anthozoan* species.

4. A construct comprising a vector and the nucleic acid according to claim 1.

5. An expression cassette comprising:
   (a) a transcriptional initiation region functional in an expression host;
   (b) the nucleic acid according to claim 1; and
   (c) a transcriptional termination region functional in said expression host.

6. An isolated host cell comprising an expression cassette according to claim 5 as part of an extrachromosomal element or integrated into the genome of a host cell as a result of introduction of said expression cassette into said host cell.

7. A method of producing a chromo- or fluorescent mutant protein, said method comprising:
   growing a cell according to claim 6, whereby said protein is expressed; and isolating said protein.

8. A kit comprising the nucleic acid according to claim 1.

* * * * *

UNITED STATES PATENT AND TRADEMARK OFFICE
CERTIFICATE OF CORRECTION

| | | |
|---|---|---|
| PATENT NO. | : 7,150,979 B2 | Page 1 of 1 |
| APPLICATION NO. | : 11/187622 | |
| DATED | : December 19, 2006 | |
| INVENTOR(S) | : Sergey Lukyanov et al. | |

It is certified that error appears in the above-identified patent and that said Letters Patent is hereby corrected as shown below:

Col. 67

In Claim 3, line 10, please replace the misspelled word "Cnidarien" with the correct spelling of --Cnidarian--.

Signed and Sealed this

Seventeenth Day of April, 2007

JON W. DUDAS
*Director of the United States Patent and Trademark Office*

SEQUENCE LISTING

<160> NUMBER OF SEQ ID NOS: 31

<210> SEQ ID NO 1
<211> LENGTH: 687
<212> TYPE: DNA
<213> ORGANISM: Anemonia majano

<400> SEQUENCE: 1

```
atggctcttt caaacaagtt tatcggagat gacatgaaaa tgacctacca tatggatggc        60
tgtgtcaatg ggcattactt taccgtcaaa ggtgaaggca acgggaagcc atacgaaggg       120
acgcagacct cgacttttaa agtcaccatg gccaacggtg ggccccttgc attctccttt       180
gacatactat ctacagtgtt caagtatgga aatcgatgct ttactgcgta tcctaccagt       240
atgcccgact atttcaaaca agcatttcct gacggaatgt catatgaaag gacttttacc       300
tatgaagatg gaggagttgc tacagccagt tgggaaataa gccttaaagg caactgcttt       360
gagcacaaat ccacgtttca tggagtgaac tttcctgctg atggacctgt gatggcgaag       420
atgacaactg gttgggaccc atcttttgag aaaatgactg tctgcgatgg aatattgaag       480
ggtgatgtca ccgcgttcct catgctgcaa ggaggtggca attacagatg ccaattccac       540
acttcttaca agacaaaaaa accggtgacg atgccaccaa accatgcggt ggaacatcgc       600
attgcgagga ccgaccttga caaaggtggc aacagtgttc agctgacgga gcacgctgtt       660
gcacatataa cctctgttgt ccctttc                                         687
```

<210> SEQ ID NO 2
<211> LENGTH: 229
<212> TYPE: PRT
<213> ORGANISM: Anemonia majano

<400> SEQUENCE: 2

```
Met Ala Leu Ser Asn Lys Phe Ile Gly Asp Asp Met Lys Met Thr Tyr
 1               5                  10                  15

His Met Asp Gly Cys Val Asn Gly His Tyr Phe Thr Val Lys Gly Glu
                20                  25                  30

Gly Asn Gly Lys Pro Tyr Glu Gly Thr Gln Thr Ser Thr Phe Lys Val
            35                  40                  45

Thr Met Ala Asn Gly Gly Pro Leu Ala Phe Ser Phe Asp Ile Leu Ser
 50                  55                  60

Thr Val Phe Lys Tyr Gly Asn Arg Cys Phe Thr Ala Tyr Pro Thr Ser
65                   70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
            115                 120                 125

Val Asn Phe Pro Ala Asp Gly Pro Val Met Ala Lys Met Thr Thr Gly
 130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Lys Pro Val Thr Met Pro
            180                 185                 190

Pro Asn His Ala Val Glu His Arg Ile Ala Arg Thr Asp Leu Asp Lys
            195                 200                 205

Gly Gly Asn Ser Val Gln Leu Thr Glu His Ala Val Ala His Ile Thr
 210                 215                 220

Ser Val Val Pro Phe
225
```

<210> SEQ ID NO 3
<211> LENGTH: 693
<212> TYPE: DNA
<213> ORGANISM: Zoanthus sp.

<400> SEQUENCE: 3

| | | | | | |
|---|---|---|---|---|---|
| atggctcagt | caaagcacgg | tctaacaaaa | gaaatgacaa | tgaaataccg | tatggaaggg | 60 |
| tgcgtcgatg | gacataaatt | tgtgatcacg | ggagagggca | ttggatatcc | gttcaagggg | 120 |
| aaacaggcta | ttaatctgtg | tgtggtcgaa | ggtggaccat | tgccatttgc | cgaagacata | 180 |
| ttgtcagctg | cctttatgta | cggaaacagg | gttttcactg | aatatcctca | agacatagct | 240 |
| gactatttca | agaactcgtg | tcctgctggt | tatacatggg | acaggtcttt | tctctttgag | 300 |
| gatggagcag | tttgcatatg | taatgcagat | ataacagtga | gtgttgaaga | aaactgcatg | 360 |
| tatcatgagt | ccaaatttta | tggagtgaat | tttcctgctg | atggacctgt | gatgaaaaag | 420 |
| atgacagata | actgggagcc | atcctgcgag | aagatcatac | cagtacctaa | gcagggata | 480 |
| ttgaagggg | atgtctccat | gtacctcctt | ctgaaggatg | gtgggcgttt | acggtgccaa | 540 |
| ttcgacacag | tttacaaagc | aaagtctgtg | ccaagaaaga | tgccggactg | gcacttcatc | 600 |
| cagcataagc | tcacccgtga | agaccgcagc | gatgctaaga | tcagaaatg | gcatctgaca | 660 |
| gaacatgcta | ttgcatccgg | atctgcattg | ccc | | | 693 |

<210> SEQ ID NO 4

<211> LENGTH: 231
<212> TYPE: PRT
<213> ORGANISM: Zoanthus sp.

<400> SEQUENCE: 4

Met Ala Gln Ser Lys His Gly Leu Thr Lys Glu Met Thr Met Lys Tyr
1               5                   10                  15

Arg Met Glu Gly Cys Val Asp Gly His Lys Phe Val Ile Thr Gly Glu
            20                  25                  30

Gly Ile Gly Tyr Pro Phe Lys Gly Lys Gln Ala Ile Asn Leu Cys Val
        35                  40                  45

Val Glu Gly Gly Pro Leu Pro Phe Ala Glu Asp Ile Leu Ser Ala Ala
    50                  55                  60

Phe Asn Tyr Gly Asn Arg Val Phe Thr Glu Tyr Pro Gln Asp Ile Ala
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Met Tyr His Glu Ser Lys Phe Tyr Gly
        115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Leu Lys Asp Gly Gly Arg
                165                 170                 175

Leu Arg Cys Gln Phe Asp Thr Val Tyr Lys Ala Lys Ser Val Pro Arg
            180                 185                 190

Lys Met Pro Asp Trp His Phe Ile Gln His Lys Leu Thr Arg Glu Asp
        195                 200                 205

Arg Ser Asp Ala Lys Asn Gln Lys Trp His Leu Thr Glu His Ala Ile
    210                 215                 220

Ala Ser Gly Ser Ala Leu Pro
225                 230

<210> SEQ ID NO 5
<211> LENGTH: 865
<212> TYPE: DNA
<213> ORGANISM: Zoanthus sp.

<400> SEQUENCE: 5
gagttgagtt tctcgacttc agttgtatca attttggggc atcaagcgat ctattttcaa     60
catggctcat tcaaagcacg gtctaaaaga gaaatgaca atgaaatacc acatggaagg    120
gtgcgtcaac ggacataaat tgtgatcac gggcgaaggc attggatatc cgttcaaagg    180
gaaacagact attaatctgt gtgtgatcga agggggacca ttgccatttt ccgaagacat    240
attgtcagct ggctttaagt acggagacag gattttcact gaatatcctc aagacatagt    300
agactatttc aagaactcgt gtcctgctgg atatacatgg ggcaggtctt ttctctttga    360
ggatggagca gtctgcatat gcaatgtaga tataacagtg agtgtcaaag aaaactgcat    420
ttatcataag agcatattta tggaatgaa ttttcctgct gatggacctg tgatgaaaaa    480
gatgacaact aactgggaag catcctgcga agatcatg ccagtaccta agcaggggat    540
actgaaaggg gatgtctcca tgtacctcct tctgaaggat ggtgggcgtt accggtgcca    600

```
gttcgacaca gtttacaaag caaagtctgt gccaagtaag atgccggagt ggcacttcat    660
ccagcataag ctcctccgtg aagaccgcag cgatgctaag aatcagaagt ggcagctgac    720
agagcatgct attgcattcc cttctgcctt ggcctgataa gaatgtagtt ccaacatttt    780
aatgcatgtg cttgtcaatt attctgataa aaatgtagtt gagttgaaaa cagacaagta    840
caaataaagc acatgtaaat cgtct                                          865
```

<210> SEQ ID NO 6
<211> LENGTH: 230
<212> TYPE: PRT
<213> ORGANISM: Zoanthus sp.

<400> SEQUENCE: 6

```
Met Ala His Ser Lys His Gly Leu Lys Glu Glu Met Thr Met Lys Tyr
 1               5                  10                  15

His Met Glu Gly Cys Val Asn Gly His Lys Phe Val Ile Thr Gly Glu
            20                  25                  30

Gly Ile Gly Tyr Pro Phe Lys Gly Lys Gln Thr Ile Asn Leu Cys Val
        35                  40                  45

Ile Glu Gly Gly Pro Leu Pro Phe Ser Glu Asp Ile Leu Ser Ala Gly
    50                  55                  60

Phe Lys Tyr Gly Asp Arg Ile Phe Thr Glu Tyr Pro Gln Asp Ile Val
65                  70                  75                  80

Asp Tyr Phe Lys Asn Ser Cys Pro Ala Gly Tyr Thr Trp Gly Ser Phe
                85                  90                  95

Leu Phe Glu Asp Gly Ala Val Cys Ile Cys Asn Val Asp Ile Thr Val
            100                 105                 110

Ser Val Lys Glu Asn Cys Ile Tyr His Lys Ser Ile Phe Asn Gly Met
        115                 120                 125

Asn Phe Pro Ala Asp Gly Pro Val Met Lys Lys Met Thr Thr Asn Trp
    130                 135                 140

Glu Ala Ser Cys Glu Lys Ile Met Pro Val Pro Lys Gln Gly Ile Leu
145                 150                 155                 160

Lys Gly Asp Val Ser Met Tyr Leu Leu Leu Lys Asp Gly Gly Arg Tyr
                165                 170                 175

Arg Cys Gln Phe Asp Thr Val Tyr Lys Ala Lys Ser Val Pro Ser Lys
            180                 185                 190

Met Pro Glu Trp His Phe Ile Gln His Lys Leu Leu Arg Glu Asp Arg
        195                 200                 205

Ser Asp Ala Lys Asn Gln Lys Trp Gln Leu Thr Glu His Ala Ile Ala
    210                 215                 220

Phe Pro Ser Ala Leu Ala
225                 230
```

<210> SEQ ID NO 7
<211> LENGTH: 678
<212> TYPE: DNA
<213> ORGANISM: Discosoma sp

<400> SEQUENCE: 7

```
atgcgctcct ccaagaacgt catcaaggag ttcatgcgct tcaaggtgcg catggagggc     60
accgtgaacg gccacgagtt cgagatcgag ggcgagggcg agggccgccc ctacgagggc    120
cacaacaccg tgaagctgaa ggtgaccaag ggcggccccc tgcccttcgc ctgggacatc    180
ctgtcccccc agttccagta cggctccaag gtgtacgtga agcaccccgc cgacatcccc    240
```

```
gactacaaga agctgtcctt ccccgagggc ttcaagtggg agcgcgtgat gaacttcgag    300
gacggcggcg tggtgaccgt gacccaggac tcctccctgc aggacggctg cttcatctac    360
aaggtgaagt tcatcggcgt gaacttcccc tccgacggcc ccgtgatgca gaagaagacc    420
atgggctggg aggcctccac cgagcgcctg taccccgcg acgcgtgct gaagggcgag     480 atccacaagg ccctgaagct gaaggacggc ggccactacc tggtggagtt caagtccatc    540
tacatggcca agaagcccgt gcagctgccc ggctactact acgtggactc caagctggac    600
atcacctccc acaacgagga ctacaccatc gtggagcagt acgagcgcac cgagggccgc    660
caccacctgt tcctgtaa                                                   678
```

<210> SEQ ID NO 8
<211> LENGTH: 225
<212> TYPE: PRT
<213> ORGANISM: Discosoma sp.

<400> SEQUENCE: 8

```
Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 9
<211> LENGTH: 696
<212> TYPE: DNA
<213> ORGANISM: Anemonia sulcata

<400> SEQUENCE: 9

```
atggcttcct ttttaaagaa gactatgccc tttaagacga ccattgaagg gacggttaat    60
```

```
ggccactact tcaagtgtac aggaaaagga gagggcaacc catttgaggg tacgcaggaa      120
atgaagatag aggtcatcga aggaggtcca ttgccatttg ccttccacat tttgtcaacg      180
agttgtatgt acggtagtaa ggccttcatc aagtatgtgt caggaattcc tgactacttc      240
aagcagtctt tccctgaagg ttttacttgg gaaagaacca caacctacga ggatggaggc      300
tttcttacag ctcatcagga cacaagccta gatggagatt gcctcgttta caaggtcaag      360
attcttggta taattttcc tgctgatggc cccgtgatgc agaacaaagc aggaagatgg      420
gagccatcca ccgagatagt ttatgaagtt gacggtgtcc tgcgtggaca gtctttgatg      480
gcccttaagt gccctggtgg tcgtcatctg acttgccatc tccatactac ttacaggtcc      540
aaaaaaccag ctgctgcctt gaagatgcca ggatttcatt ttgaagatca tcgcatcgag      600
ataatggagg aagttgagaa aggcaagtgc tataaacagt acgaagcagc agtgggcagg      660
tactgtgatg ctgctccatc caagcttgga cataac                              696

<210> SEQ ID NO 10
<211> LENGTH: 232
<212> TYPE: PRT
<213> ORGANISM: Anemonia sulcata

<400> SEQUENCE: 10

Met Ala Ser Phe Leu Lys Lys Thr Met Pro Phe Lys Thr Thr Ile Glu
1               5                   10                  15

Gly Thr Val Asn Gly His Tyr Phe Lys Cys Thr Gly Lys Gly Glu Gly
            20                  25                  30

Asn Pro Phe Glu Gly Thr Gln Glu Met Lys Ile Glu Val Ile Glu Gly
        35                  40                  45

Gly Pro Leu Pro Phe Ala Phe His Ile Leu Ser Thr Ser Cys Met Tyr
    50                  55                  60

Gly Ser Lys Thr Phe Ile Lys Tyr Val Ser Gly Ile Pro Asp Tyr Phe
65                  70                  75                  80

Lys Gln Ser Phe Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110

Asp Cys Leu Val Tyr Lys Val Lys Ile Leu Gly Asn Asn Phe Pro Ala
        115                 120                 125

Asp Gly Pro Val Met Gln Asn Lys Ala Gly Arg Trp Glu Pro Ala Thr
    130                 135                 140

Glu Ile Val Tyr Glu Val Asp Gly Val Leu Arg Gly Gln Ser Leu Met
145                 150                 155                 160

Ala Leu Lys Cys Pro Gly Gly Arg His Leu Thr Cys His Leu His Thr
                165                 170                 175

Thr Tyr Arg Ser Lys Lys Pro Ala Ala Ala Leu Lys Met Pro Gly Phe
            180                 185                 190

His Phe Glu Asp His Arg Ile Glu Ile Met Glu Glu Val Glu Lys Gly
        195                 200                 205

Lys Cys Tyr Lys Gln Tyr Glu Ala Ala Val Gly Arg Tyr Cys Asp Ala
    210                 215                 220

Ala Pro Ser Lys Leu Gly His Asn
225                 230

<210> SEQ ID NO 11
<211> LENGTH: 678
<212> TYPE: DNA
```

<213> ORGANISM: Artificial Sequence
<220> FEATURE:
<223> OTHER INFORMATION: hybrid coding sequence

<400> SEQUENCE: 11

```
atgagctgca gcaagaacgt gatcaaggag ttcatgcggt tcaaggtgcg gatggagggc      60
accgtgaacg gccacgagtt cgagatcaag ggcgagggcg agggccggcc ctacgagggc     120
cactgcagcg tgaagctcat ggtgaccaag ggcggccccc tcccttcgc cttcgacatc      180
ctcagccccc agttccagta cggcagcaag gtgtacgtga agcaccccgc cgacatcccc     240
gactacaaga agctcagctt ccccgagggc ttcaagtggg agcgggtgat gaacttcgag     300
gacggcggcg tggtgaccgt gagccaggac agcagcctca aggacggctg cttcatctac     360
gaggtgaagt tcatcggcgt gaacttcccc agcgacggcc ccgtgatgca gcggcggacc     420
cggggctggg aggccagcag cgagcggctc taccccgggg acggcgtgct caagggcgac     480
atccacatgg ccctccggct cgaggcggc ggccactacc tcgtggagtt caagagcatc      540
tacatggcca agaagcccgt gcagctcccc ggctactact acgtggacag caagctcgac     600
atcaccagcc acaacgagga ctacaccatc gtggagcagt acgagcggac cgagggccgg     660
caccacctct tcctctga                                                    678
```

<210> SEQ ID NO 12
<211> LENGTH: 225
<212> TYPE: PRT
<213> ORGANISM: Artificial Sequence
<220> FEATURE:
<223> OTHER INFORMATION: hybrid protein

<400> SEQUENCE: 12

```
Met Ser Cys Ser Lys Asn Val Ile Lys Glu Phe Met Arg Phe Lys Val
 1               5                  10                  15

Arg Met Glu Gly Thr Val Asn Gly His Glu Phe Glu Ile Lys Gly Glu
            20                  25                  30

Gly Glu Gly Arg Pro Tyr Glu Gly His Cys Ser Val Lys Leu Met Val
        35                  40                  45

Thr Lys Gly Gly Pro Leu Pro Phe Ala Phe Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Ser Gln Asp Ser Ser
            100                 105                 110

Leu Lys Asp Gly Cys Phe Ile Tyr Glu Val Lys Phe Ile Gly Val Asn
        115                 120                 125

Phe Pro Ser Asp Gly Pro Val Met Gln Arg Arg Thr Arg Gly Trp Glu
    130                 135                 140

Ala Ser Ser Glu Arg Leu Tyr Pro Arg Asp Gly Val Leu Lys Gly Asp
145                 150                 155                 160

Ile His Met Ala Leu Arg Leu Glu Gly Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205
```

-continued

```
Thr Ile Val Glu Gln Tyr Glu Arg Thr Glu Gly Arg His His Leu Phe
    210                 215                 220
Leu
225

<210> SEQ ID NO 13
<211> LENGTH: 675
<212> TYPE: DNA
<213> ORGANISM: Artificial Sequence
<220> FEATURE:
<223> OTHER INFORMATION: non-aggregating mutant

<400> SEQUENCE: 13
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagctgaa ggtgaccaag ggcggccccc tgcccttcgc ctgggacatc     180 ctgtccccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccccgcg acggcgtgct gaagggcgag     480
acccacaagg ccctgaagct gaaggacggc ggccactacc tggtggagtt caagtccatc     540
tacatggcca agaagcccgt gcagctgccc ggctactact acgtggacgc caagctggac     600
atcacctccc acaacgagga ctacaccatc gtggagcagt acgagcgcac cgagggccgc     660
caccacctgt cctg                                                        675

<210> SEQ ID NO 14
<211> LENGTH: 678
<212> TYPE: DNA
<213> ORGANISM: Artificial Sequence
<220> FEATURE:
<223> OTHER INFORMATION: non-aggregating mutant

<400> SEQUENCE: 14
atggcctcct ccgagaacgt catcaccgag ttcatgcgct tcaaggtgcg catggagggc      60
accgtgaacg gccacgagtt cgagatcgag ggcgagggcg agggccgccc ctacgagggc     120
cacaacaccg tgaagttgaa ggtgaccaag ggcggccccc tgcccttcgc ctgggacatc     180 ctgtccccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccccgcg acggcgtgct gaagggcgag     480
atccacaagg ccctgaagct gaaggacggc ggccactacc tggtggagtt caagtccatc     540
tacatggcca agaagcccgt gcagctgccc ggctactact acgtggacac caagctggac     600
atcacctccc acaacgagga ctacaccatc gtggagcagt acgagcgcac cgagggccgc     660
caccacctgt cctgtaa                                                     678

<210> SEQ ID NO 15
<211> LENGTH: 705
<212> TYPE: DNA
<213> ORGANISM: Artificial Sequence
```

-continued

```
<220> FEATURE:
<223> OTHER INFORMATION: non-aggregating mutant

<400> SEQUENCE: 15
ggatccgctc agtcagagca cggtctaaca gaagaaatga caatgaaata ccgtatggaa      60
gggtgcgtcg atggacataa atttgtgatc acgggagagg gcattggata tccgttcaaa     120 ggaaacagg ctattaatct gtgtgtggtc gaaggtggac cattgccatt tgccgaagac      180
atattgtcag ctgcctttat gtacggaaac agggttttca ctgaatatcc tcaagacata    240
gttgactatt tcaagaactc gtgtcctgct ggatatacat gggacaggtc ttttctcttt    300
gaggatggag cagtttgcat atgtaatgca gatataacag tgagtgttga agaaaactgc    360
atgtatcatg agtccaaatt ctatggagtg aatttcctg ctgatggacc tgtgatgaaa     420
aagatgacag ataactggga gccatcctgc gagaagatca taccagtacc taagcagggg    480
atattgaaag gggatgtctc catgtacctc cttctgaagg atggtgggcg tttacggtgc    540
caattcgaca cagtttacaa agcaaagtct gtgccaagaa agatgccgga ctggcacttc    600
atccagcata agctcacccg tgaagaccgc agcgatgcta agaatcagaa atggcatctg    660
acagaacatg ctattgcatc cggatctgca ttgccctgaa agctt                     705

<210> SEQ ID NO 16
<211> LENGTH: 230
<212> TYPE: PRT
<213> ORGANISM: Artificial Sequence
<220> FEATURE:
<223> OTHER INFORMATION: non-aggregating mutant

<400> SEQUENCE: 16

Ala His Ser Glu His Gly Leu Thr Glu Glu Met Thr Met Lys Tyr His
 1               5                  10                  15

Met Glu Gly Cys Val Asn Gly His Lys Phe Val Ile Thr Gly Glu Gly
             20                  25                  30

Ile Gly Tyr Pro Phe Lys Gly Lys Gln Thr Ile Asn Leu Cys Val Ile
         35                  40                  45

Glu Gly Gly Pro Leu Pro Phe Ser Glu Asp Ile Leu Ser Ala Gly Phe
     50                  55                  60

Lys Tyr Gly Asp Arg Ile Phe Thr Glu Tyr Pro Gln Asp Ile Val Asp
 65                  70                  75                  80

Tyr Phe Lys Asn Ser Cys Pro Ala Gly Tyr Thr Trp Gly Arg Ser Phe
                 85                  90                  95

Leu Phe Glu Asp Gly Ala Val Cys Ile Cys Asn Val Asp Ile Thr Val
            100                 105                 110

Ser Val Lys Glu Asn Cys Ile Tyr His Lys Ser Ile Phe Asn Gly Val
        115                 120                 125

Asn Phe Pro Ala Asp Gly Pro Val Met Lys Met Thr Thr Asn Trp
    130                 135                 140

Glu Ala Ser Cys Glu Lys Ile Met Pro Val Pro Lys Gln Gly Ile Leu
145                 150                 155                 160

Lys Gly Asp Val Ser Met Tyr Leu Leu Lys Asp Gly Gly Arg Tyr
                165                 170                 175

Arg Cys Gln Phe Asp Thr Val Tyr Lys Ala Lys Ser Val Pro Ser Lys
            180                 185                 190

Met Pro Glu Trp His Phe Ile Gln His Lys Leu Leu Arg Glu Asp Arg
        195                 200                 205

Ser Asp Ala Lys Asn Gln Lys Trp Gln Leu Thr Glu His Ala Ile Ala
```

-continued

```
                  210                 215                 220

Phe Pro Ser Ala Leu Ala
225                 230

<210> SEQ ID NO 17
<211> LENGTH: 705
<212> TYPE: DNA
<213> ORGANISM: Artificial Sequence
<220> FEATURE:
<223> OTHER INFORMATION: non-aggregating mutant

<400> SEQUENCE: 17
ggatccgccc acagcgagca cggcctgacc gaggagatga ccatgaagta ccacatggag      60
ggctgcgtga acggccacaa gttcgtgatc accggcgagg gcatcggcta ccccttcaag     120
ggcaagcaga ccatcaacct gtgcgtgatc gagggcggcc ccctgccctt cagcgaggac     180
atcctgagcg ccggcttcaa gtacggcgac cggatcttca ccgagtaccc ccaggacatc     240
gtggactact tcaagaacag ctgccccgcc ggctacacct ggggccggag cttcctgttc     300
gaggacggcg ccgtgtgcat ctgtaacgtg gacatcaccg tgagcgtgaa ggagaactgc     360
atctaccaca gagcatcttt caacggcgtg aacttccccg ccgacggccc cgtgatgaag     420
aagatgacca ccaactggga ggccagctgc gagaagatca tgcccgtgcc taagcagggc     480
atcctgaagg gcgacgtgag catgtacctg ctgctgaagg acgcggccg gtaccggtgc     540 cagttcgaca ccgtgtacaa ggccaagagc gtgcccagca agatgcccga gtggcacttc     600
atccagcaca agctgctgcg ggaggaccgg agcgacgcca gaaccagaa gtggcagctg     660 accgagcacg ccatcgcctt ccccagcgcc ctggcctgaa agctt                     705

<210> SEQ ID NO 18
<211> LENGTH: 230
<212> TYPE: PRT
<213> ORGANISM: Artificial Sequence
<220> FEATURE:
<223> OTHER INFORMATION: non-aggregating mutant

<400> SEQUENCE: 18

Ala His Ser Glu His Gly Leu Thr Glu Glu Met Thr Met Lys Tyr His
1               5                   10                  15

Met Glu Gly Cys Val Asn Gly His Lys Phe Val Ile Thr Gly Glu Gly
            20                  25                  30

Ile Gly Tyr Pro Phe Lys Gly Lys Gln Thr Ile Asn Leu Cys Val Ile
        35                  40                  45

Glu Gly Gly Pro Leu Pro Phe Ser Glu Asp Ile Leu Ser Ala Gly Phe
    50                  55                  60

Lys Tyr Gly Asp Arg Ile Phe Thr Glu Tyr Pro Gln Asp Ile Val Asp
65                  70                  75                  80

Tyr Phe Lys Asn Ser Cys Pro Ala Gly Tyr Thr Trp Gly Arg Ser Phe
                85                  90                  95

Leu Phe Glu Asp Gly Ala Val Cys Ile Cys Asn Val Asp Ile Thr Val
            100                 105                 110

Ser Val Lys Glu Asn Cys Ile Tyr His Lys Ser Ile Phe Asn Gly Val
        115                 120                 125

Asn Phe Pro Ala Asp Gly Pro Val Met Lys Met Thr Thr Asn Trp
    130                 135                 140

Glu Ala Ser Cys Glu Lys Ile Met Pro Val Pro Lys Gln Gly Ile Leu
145                 150                 155                 160
```

```
Lys Gly Asp Val Ser Met Tyr Leu Leu Leu Lys Asp Gly Arg Tyr
            165                 170                 175

Arg Cys Gln Phe Asp Thr Val Tyr Lys Ala Lys Ser Val Pro Ser Lys
            180                 185                 190

Met Pro Glu Trp His Phe Ile Gln His Lys Leu Leu Arg Glu Asp Arg
            195                 200                 205

Ser Asp Ala Lys Asn Gln Lys Trp Gln Leu Thr Glu His Ala Ile Ala
            210                 215                 220

Phe Pro Ser Ala Leu Ala
225                 230

<210> SEQ ID NO 19
<211> LENGTH: 690
<212> TYPE: DNA
<213> ORGANISM: Artificial Sequence
<220> FEATURE:
<223> OTHER INFORMATION: non-aggregating mutant

<400> SEQUENCE: 19
atggccctgt ccaacgagtt catcggcgac gacatgaaga tgacctacca catggacggc      60
tgcgtgaacg gccactactt caccgtgaag ggcgagggca gcggcaagcc ctacgagggc     120
acccagacct ccaccttcaa ggtgaccatg gccaacggcg cccctggc cttctccttc       180 gacatcctgt ccaccgtgtt catgtacggc aaccgctgct tcaccgccta ccccaccagc    240
atgcccgact acttcaagca ggccttcccc gacggcatgt cctacgagag aaccttcacc    300
tacgaggacg gcgccgtggc caccgccagc tgggagatca gcctgaaggg caactgcttc    360
gagcacaagt ccaccttcca cggcgtgaac ttccccgccg acggccccgt gatggccaag    420
aagaccaccg ctgggacccc tccttcgag aagatgaccg tgtgcgacgg catcttgaag    480
ggcgacgtga ccgccttcct gatgctgcag ggcggcggca actacagatg ccagttccac    540
acctcctaca agaccaagaa gcccgtgacc atgcccccca ccacgtggt ggagcaccgc    600 atcgccagaa ccgacctgga caagggcggc aacagcgtgc agctgaccga gcacgccgtg    660
gcccacatca cctccgtggt gcccttctga                                     690

<210> SEQ ID NO 20
<211> LENGTH: 229
<212> TYPE: PRT
<213> ORGANISM: Artificial Sequence
<220> FEATURE:
<223> OTHER INFORMATION: non-aggregating mutant

<400> SEQUENCE: 20

Met Ala Leu Ser Asn Glu Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
            35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110
```

```
Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
        130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Lys Pro Val Thr Met Pro
            180                 185                 190

Pro Asn His Val Val Glu His Arg Ile Ala Arg Thr Asp Leu Asp Lys
        195                 200                 205

Gly Gly Asn Ser Val Gln Leu Thr Glu His Ala Val Ala His Ile Thr
        210                 215                 220

Ser Val Val Pro Phe
225

<210> SEQ ID NO 21
<211> LENGTH: 707
<212> TYPE: DNA
<213> ORGANISM: Artificial Sequence
<220> FEATURE:
<223> OTHER INFORMATION: non-aggregating mutant

<400> SEQUENCE: 21
ggatccgcct ccctgctgac cgagaccatg cccttcagga ccaccatcga gggcaccgtg      60
aacggccact acttcaagtg caccggcaag ggcgagggca ccccctcga gggcacccag      120 gagatgaaga tcgaggtgat cgagggcggc cccctgccct cgccttcca catcctgtcc      180 acctcctgca tgtacggctc caaggccttc atcaagtacg tgtccggcat ccccgactac      240
ttcaagcagt ccctccccga gggcttcacc tgggagcgca ccaccaccta cgaggacggc      300
ggcttcctga ccgcccacca ggacacctcc ctggacggcg actgctggt gtacaaggtg      360 aagatcctgg gcaacaactt ccccgccgac ggccccgtga tgcagaacaa ggccggccgc      420
tgggagccct ccaccgagat cgtgtacgag gtggacggcg tgctgcgcgg ccagtccctg      480
atggccctgg agtgccccgg cggtcgccac ctgacctgcc acctgcacac cacctaccgc      540
tccaagaagc ccgcctccgc cctgaagatg cccggcttcc acttcgagga ccaccgcatc      600
gagatcctgg aggaggtgga agggcaag tgctacaagc agtacgaggc cgccgtgggc      660
cgctactgcg acgccgcccc ctccaagctg ggccacaact gaagctt                    707

<210> SEQ ID NO 22
<211> LENGTH: 231
<212> TYPE: PRT
<213> ORGANISM: Artificial Sequence
<220> FEATURE:
<223> OTHER INFORMATION: non-aggregating mutant

<400> SEQUENCE: 22

Ala Ser Leu Leu Thr Glu Thr Met Pro Phe Arg Thr Thr Ile Glu Gly
  1               5                  10                  15

Thr Val Asn Gly His Tyr Phe Lys Cys Thr Gly Lys Gly Glu Gly Asn
                20                  25                  30

Pro Leu Glu Gly Thr Gln Glu Met Lys Ile Glu Val Ile Glu Gly Gly
            35                  40                  45

Pro Leu Pro Phe Ala Phe His Ile Leu Ser Thr Ser Cys Met Tyr Gly
```

```
                     50                  55                  60
Ser Lys Ala Phe Ile Lys Tyr Val Ser Gly Ile Pro Asp Tyr Phe Lys
 65                  70                  75                  80

Gln Ser Leu Pro Glu Gly Phe Thr Trp Glu Arg Thr Thr Thr Tyr Glu
                 85                  90                  95

Asp Gly Gly Phe Leu Thr Ala His Gln Asp Thr Ser Leu Asp Gly Asp
                100                 105                 110

Cys Leu Val Tyr Lys Val Lys Ile Leu Gly Asn Asn Phe Pro Ala Asp
                115                 120                 125

Gly Pro Val Met Gln Asn Lys Ala Gly Arg Trp Glu Pro Ser Thr Glu
            130                 135                 140

Ile Val Tyr Glu Val Asp Gly Val Leu Arg Gly Gln Ser Leu Met Ala
145                 150                 155                 160

Leu Glu Cys Pro Gly Gly Arg His Leu Thr Cys His Leu His Thr Thr
                165                 170                 175

Tyr Arg Ser Lys Lys Pro Ala Ser Ala Leu Lys Met Pro Gly Phe His
            180                 185                 190

Phe Glu Asp His Arg Ile Glu Ile Leu Glu Glu Val Glu Lys Gly Lys
            195                 200                 205

Cys Tyr Lys Gln Tyr Glu Ala Ala Val Gly Arg Tyr Cys Asp Ala Ala
        210                 215                 220

Pro Ser Lys Leu Gly His Asn
225                 230

<210> SEQ ID NO 23
<211> LENGTH: 654
<212> TYPE: DNA
<213> ORGANISM: Artificial Sequence
<220> FEATURE:
<223> OTHER INFORMATION: non-aggregating mutant

<400> SEQUENCE: 23
gagggcaccg tgaacggcca ctacttcaag tgcaccggca agggcgaggg caaccccctc     60
gagggcaccc aggagatgaa gatcgaggtg atcgagggcg gccccctgcc cttcgccttc    120
cacatcctgt ccacctcctg catgtacggc tccaaggcct tcatcaagta cgtgtccggc    180
atccccgact acttcaagca gtccctcccc gagggcttca cctgggagcg caccaccacc    240
tacgaggacg gcggcttcct gaccgcccac caggacacct ccctggacgg cgactgcctg    300
gtgtacaagg tgaagatcct gggcaacaac ttccccgccg acggccccgt gatgcagaac    360
aaggccggcc gctgggagcc ctccaccgag atcgtgtacg aggtggacgg cgtgctgcgc    420
ggccagtcca gcatggccct ggagtgcccc ggcggtcgcc acctgacctg ccacctgcac    480
accacctacc gctccaagaa gcccgcctcc gccctgaaga tgcccggctt ccacttcgag    540
gaccaccgca tcgagatcct ggaggaggtg gagaagggca agtgctacaa gcagtacgag    600
gccgccgtgg gccgctactg cgacgccgcc ccctccaagc tgggccacaa ctga          654

<210> SEQ ID NO 24
<211> LENGTH: 232
<212> TYPE: PRT
<213> ORGANISM: Artificial Sequence
<220> FEATURE:
<223> OTHER INFORMATION: non-aggregating mutant

<400> SEQUENCE: 24

Met Ala Ser Leu Leu Thr Glu Thr Met Pro Phe Arg Thr Thr Ile Glu
 1               5                  10                  15
```

-continued

```
Gly Thr Val Asn Gly His Tyr Phe Lys Cys Thr Gly Lys Gly Glu Gly
            20                  25                  30

Asn Pro Leu Glu Gly Thr Gln Glu Met Lys Ile Glu Val Ile Glu Gly
            35                  40                  45

Gly Pro Leu Pro Phe Ala Phe His Ile Leu Ser Thr Ser Cys Met Tyr
            50                  55                  60

Gly Ser Lys Ala Phe Ile Lys Tyr Val Ser Gly Ile Pro Asp Tyr Phe
65                  70                  75                  80

Lys Gln Ser Leu Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110

Asp Cys Leu Val Tyr Lys Val Lys Ile Leu Gly Asn Asn Phe Pro Ala
            115                 120                 125

Asp Gly Pro Val Met Gln Asn Lys Ala Gly Arg Trp Glu Pro Ser Thr
            130                 135                 140

Glu Ile Val Tyr Glu Val Asp Gly Val Leu Arg Gly Gln Ser Ser Met
145                 150                 155                 160

Ala Leu Glu Cys Pro Gly Gly Arg His Leu Thr Cys His Leu His Thr
                165                 170                 175

Thr Tyr Arg Ser Lys Lys Pro Ala Ser Ala Leu Lys Met Pro Gly Phe
            180                 185                 190

His Phe Glu Asp His Arg Ile Glu Ile Leu Glu Glu Val Gly Lys Gly
            195                 200                 205

Lys Cys Tyr Lys Gln Tyr Glu Ala Ala Val Gly Arg Tyr Cys Asp Ala
210                 215                 220

Ala Pro Ser Lys Leu Gly His Asn
225                 230

<210> SEQ ID NO 25
<211> LENGTH: 26
<212> TYPE: PRT
<213> ORGANISM: Artificial Sequence
<220> FEATURE:
<223> OTHER INFORMATION: non-aggregating mutant fragment

<400> SEQUENCE: 25

Met Arg Ser Ser Lys Asn Val Ile Lys Glu Phe Met Arg Phe Lys Val
1               5                   10                  15

Arg Met Glu Gly Thr Val Asn Gly His Glu
            20                  25

<210> SEQ ID NO 26
<211> LENGTH: 26
<212> TYPE: PRT
<213> ORGANISM: Artificial Sequence
<220> FEATURE:
<223> OTHER INFORMATION: non-aggregating mutant fragment

<400> SEQUENCE: 26

Met Ser Cys Ser Lys Asn Val Ile Lys Glu Phe Met Arg Phe Gln Val
1               5                   10                  15

Arg Met Glu Gly Thr Val Asn Gly His Glu
            20                  25

<210> SEQ ID NO 27
<211> LENGTH: 26
<212> TYPE: PRT
```

<213> ORGANISM: Artificial Sequence
<220> FEATURE:
<223> OTHER INFORMATION: non-aggregating mutant fragment

<400> SEQUENCE: 27

Met Ala Gln Ser Lys His Gly Leu Thr Lys Glu Met Thr Met Lys Tyr
 1               5                  10                  15

Arg Met Glu Gly Cys Val Asp Gly His Lys
            20                  25

<210> SEQ ID NO 28
<211> LENGTH: 26
<212> TYPE: PRT
<213> ORGANISM: Artificial Sequence
<220> FEATURE:
<223> OTHER INFORMATION: non-aggregating mutant fragment

<400> SEQUENCE: 28

Met Ala His Ser Lys His Gly Leu Lys Glu Glu Met Thr Met Lys Tyr
 1               5                  10                  15

His Met Glu Gly Cys Val Asn Gly His Lys
            20                  25

<210> SEQ ID NO 29
<211> LENGTH: 26
<212> TYPE: PRT
<213> ORGANISM: Artificial Sequence
<220> FEATURE:
<223> OTHER INFORMATION: non-aggregating mutant fragment

<400> SEQUENCE: 29

Met Ala Leu Ser Asn Lys Phe Ile Gly Asp Asp Met Lys Met Thr Tyr
 1               5                  10                  15

His Met Asp Gly Cys Val Asn Gly His Tyr
            20                  25

<210> SEQ ID NO 30
<211> LENGTH: 23
<212> TYPE: PRT
<213> ORGANISM: Artificial Sequence
<220> FEATURE:
<223> OTHER INFORMATION: non-aggregating mutant fragment

<400> SEQUENCE: 30

Met Ala Ser Phe Leu Lys Lys Thr Met Pro Phe Lys Thr Thr Ile Glu
 1               5                  10                  15

Gly Thr Val Asn Gly His Tyr
            20

<210> SEQ ID NO 31
<211> LENGTH: 10
<212> TYPE: PRT
<213> ORGANISM: Artificial Sequence
<220> FEATURE:
<223> OTHER INFORMATION: purification tag

<400> SEQUENCE: 31

Met Arg His His His His His His Gly Ser
 1               5                  10